(12) United States Patent
Johnson et al.

(10) Patent No.: US 11,700,494 B2
(45) Date of Patent: Jul. 11, 2023

(54) HEARING AID CONNECTOR

(71) Applicant: Earlens Corporation, Menlo Park, CA (US)

(72) Inventors: Eric B. Johnson, Mountain View, CA (US); Vincent W. Ku, Palo Alto, CA (US); Patricia Ho, Redwood City, CA (US); Ryan Lane-Lutter, Redwood City, CA (US); Daniel K. Hallock, Redwood City, CA (US)

(73) Assignee: Earlens Corporation, Menlo Park, CA (US)

( * ) Notice: Subject to any disclaimer, the term of this patent is extended or adjusted under 35 U.S.C. 154(b) by 0 days.

(21) Appl. No.: 17/689,782

(22) Filed: Mar. 8, 2022

(65) Prior Publication Data

US 2023/0024347 A1   Jan. 26, 2023

Related U.S. Application Data

(63) Continuation of application No. 16/272,677, filed on Feb. 11, 2019, now Pat. No. 11,310,611, which is a
(Continued)

(51) Int. Cl.
*H04R 25/00* (2006.01)
*H01R 43/20* (2006.01)
(Continued)

(52) U.S. Cl.
CPC ......... *H04R 25/609* (2019.05); *A61N 1/0526* (2013.01); *H01R 12/714* (2013.01); *H01R 13/4226* (2013.01); *H01R 43/20* (2013.01); *H04R 25/607* (2019.05); *H01R 2201/12* (2013.01); *H04R 2225/025* (2013.01);
(Continued)

(58) Field of Classification Search
CPC .... H04R 23/008; H04R 25/60; H04R 25/607; H04R 25/609; H04R 25/656; H04R 25/658; H04R 2225/0213; H04R 2225/0216; H04R 2225/025; H04R 2225/57; H04R 2460/11; A61N 1/0526
See application file for complete search history.

(56) References Cited

U.S. PATENT DOCUMENTS 5,572,594 A * 11/1996 Devoe ............... H04R 25/656
                                                       381/328
7,016,512 B1 * 3/2006 Feeley ................. H04R 1/10
                                                       381/322
(Continued)

*Primary Examiner* — Huyen D Le
(74) *Attorney, Agent, or Firm* — Polsinelli PC

(57) ABSTRACT

In embodiments of the invention, the invention comprises a light tip cable including a cartridge assembly affixed to a medial end of the cable, the cartridge assembly including an emitter housing where the emitter housing includes an opening at a medial end of the housing and a flange at a lateral end of the housing. In embodiments of the invention, the cartridge assembly includes a light emitting element in the housing extending to the opening, retention features covering at least a portion of the housing, including the flange, the retention features comprising a lateral face and a lobe and at least one load bearing strand extending from the cable to the emitter; and electrical connectors extending from the cable to the light emitting element.

17 Claims, 25 Drawing Sheets

Related U.S. Application Data continuation of application No. PCT/US2017/046748, filed on Aug. 14, 2017.

(60) Provisional application No. 62/466,634, filed on Mar. 3, 2017, provisional application No. 62/375,284, filed on Aug. 15, 2016.

(51) Int. Cl.
*H01R 13/422* (2006.01)
*A61N 1/05* (2006.01)
*H01R 12/71* (2011.01)

(52) U.S. Cl.
CPC ............ *H04R 2225/0213* (2019.05); *H04R 2225/0216* (2019.05); *H04R 2225/57* (2019.05); *H04R 2460/11* (2013.01)

(56) References Cited

U.S. PATENT DOCUMENTS

| 10,034,103 B2 * | 7/2018 | Puria | H04R 25/456 |
| 2009/0304216 A1 * | 12/2009 | Hansen | H04R 25/604 |
| | | | 381/324 |

\* cited by examiner

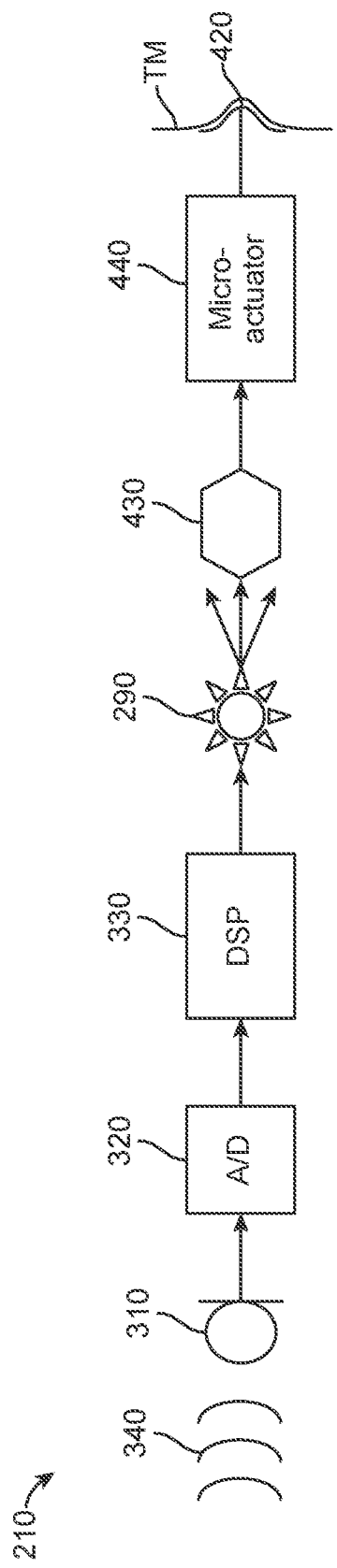

HEARING AID CONNECTOR

CROSS-REFERENCE

This application is a continuation of U.S. patent application Ser. No. 16/272,677, filed Feb. 11, 2019, now U.S. Pat. No. 11,310,611; which is a continuation of PCT Application No. PCT/US17/46748, filed Aug. 14, 2017; which claims priority to U.S. Provisional Application No. 62/375,284, filed Aug. 15, 2016, and U.S. Provisional Application No. 62/466,634, filed Mar. 3, 2017; which are incorporated herein by reference in its entirety and to which priority is claimed under 35 U.S.C. § 120.

FIELD OF THE INVENTION

The present invention is related to a replaceable eartip tip for use in hearing aids and, more particularly, to a replaceable light tip for use in contact hearing aids hearing aids.

BACKGROUND OF THE INVENTIION

In hearing aids, external processors, otherwise known as behind the ear components or BTEs, are connected to internal components, also known as eartips or light tips, by an electrical cable which plugs into the BTE. At the opposite end of the electrical cable is a transmission element which fits into the ear of a user. The transmission element then transmits information to the user in the form of, for example, audible sound, light, radio frequency transmissions, or magnetic transmissions. In some designs, the transmission element may be placed in a custom ear tip which is designed to conform to the user's ear canal.

SUMMARY OF THE INVENTION

In the present invention, a custom ear tip is designed to be removable and replicable. In particular, the custom ear tip is designed such that it can be easily attached to and removed from a transmission element at the end of an electrical cable which is connected to a BTE. A health care professional may use the ability to quickly and easily replace the ear tip to provide the user with a selection of ear tips in order to, for example, select the most comfortable ear tip for the individual user.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale; emphasis instead being placed upon illustrating the principles of the preferred embodiments.

FIG. 2 is a block diagram of the components of a hearing aid system according to the present invention.

DETAILED DESCRIPTION OF THE INVENTION

Figure 1:
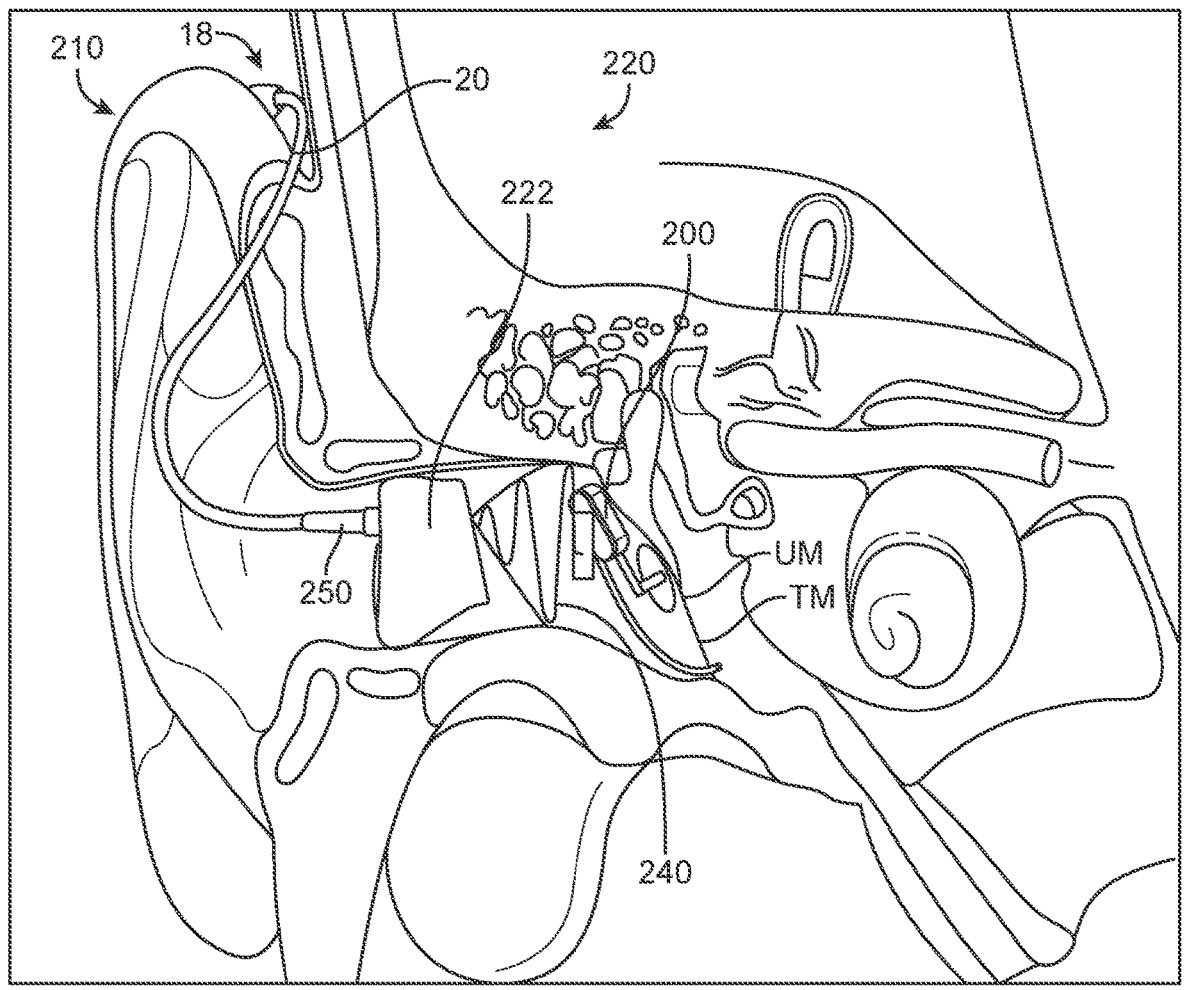
FIG. 1 is a schematic illustration of a hearing aid system including a contact hearing device according to the present invention.

FIG. 1 is a schematic illustration of a hearing aid system 210, including a contact hearing device 220 according to the present invention. In FIG. 1, BTE 18 is connected to light tip 222 by LT cable 20, which may include a taper tube 250. Light tip 222 is adapted to radiate light pulses 240 to tympanic lens 200 which is positioned on or adjacent a user's tympanic membrane TM in a manner which allows it to drive the user's umbo UM directly.

FIG. 2 is a block diagram of a hearing aid system 210 according to the present invention. In FIG. 2, sound 340 is detected by microphone 310, which is connected to analog to digital converter 320. Sound signals processed by analog to digital converter 320 are transmitted to digital signal processor 330. Digital signal processor 330 is, in turn, connected to emitter 290, which radiates light to photodetector 430. The output of photodetector 430 drives microactuator 440, which includes umbo lens 420. Umbo lens 220 is positioned on a user's tympanic membrane TM in a manner which allows it to move the user's tympanic membrane directly.

In embodiments of the invention an electromagnetic transmitter may be substituted for emitter 290 and an electromagnetic receiver may be substituted for photodetector 430 such that the signal transmitted may be a signal such as, a radio frequency or magnetically coupled signal.

Figure 2A:
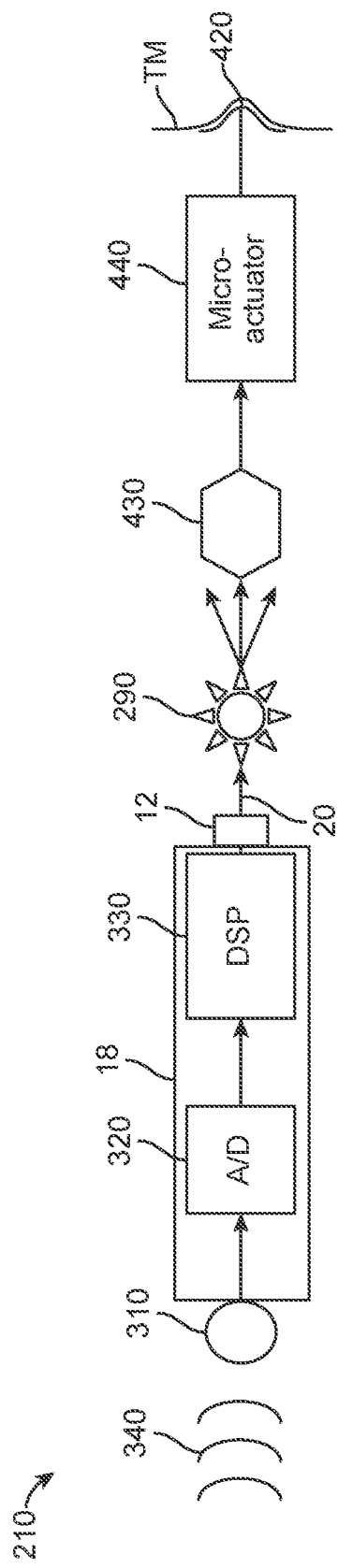
FIG. 2A is a block diagram of the components of a hearing aid system according to the present invention.

FIG. 2A is a block diagram of the components of a hearing aid system 210 according to the present invention. In FIG. 2A, sound 340 is detected by microphone 310, which is connected to analog to digital converter 320. Sound signals processed by analog to digital converter 320 are transmitted to digital signal processor 330. Microphone 310, analog to digital converter 320 and digital signal processor 330 combine to form BTE 18, which may also be referred to as an audio processor. In FIG. 2A, BTE 18 is connected to emitter 290 through LT cable 20, which is connected to audio processor 230 by light tip connector 12. Emitter 290 radiates light to photodetector 430. The output of photodetector 430 drives microactuator 440, which, in turn, drives umbo lens 420. Umbo lens 220 is positioned on a user's tympanic membrane TM in a manner which allows it to move the user's tympanic membrane directly.

Figure 3:
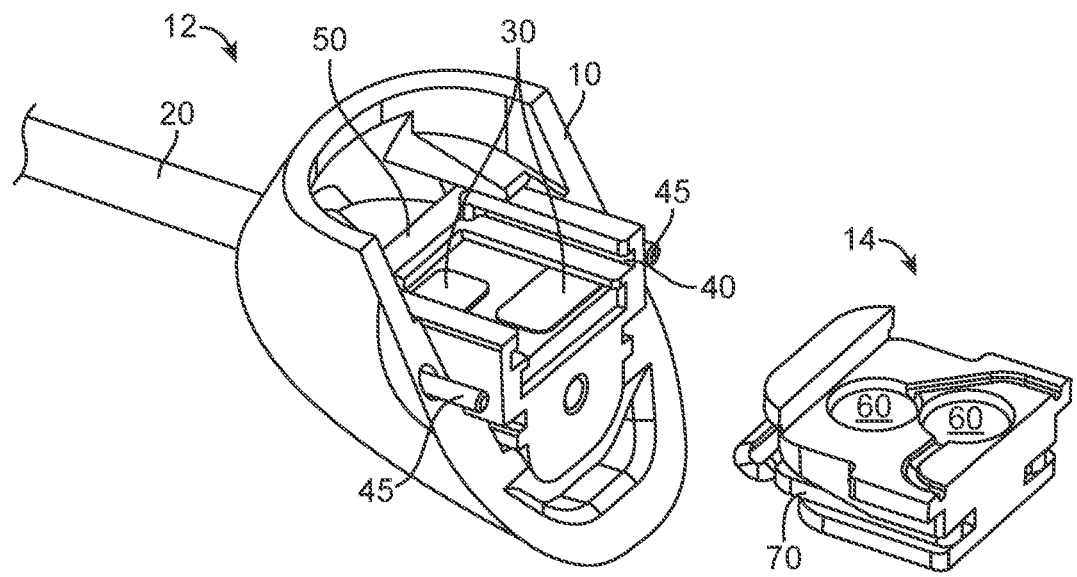
FIG. 3 is a perspective view of a lateral end of a light tip connector and the internal assembly of a BTE connector according to the present invention.

FIG. 3 is a perspective view of a medial end of a light tip connector 12 according to the present invention. FIG. 3 further includes a view of an internal assembly 14 of a BTE connector (not shown) according to the present invention. In FIG. 3, LT housing 10 (which may also be referred to as a light tip housing 10) is connected to LT cable 20 (which may also be referred to as a light tip cable 20). LT housing 10 further includes LT electrodes 30 (which may also be referred to as light tip electrodes 30), guide channel 40, guide pins 45, and locking pin 50. Internal assembly 14 in FIG. 3 is an internal assembly of a BTE connector 16 (not shown), which includes pogo pin electrodes 60 and latch 70. In embodiments of the invention, LT housing 10 may include one or more additional electrodes 30 and internal assembly 14 may include one or more additional pogo pin electrodes 60 depending upon the number of wires needed to transmit signals through LT cable 20.

Figure 4:
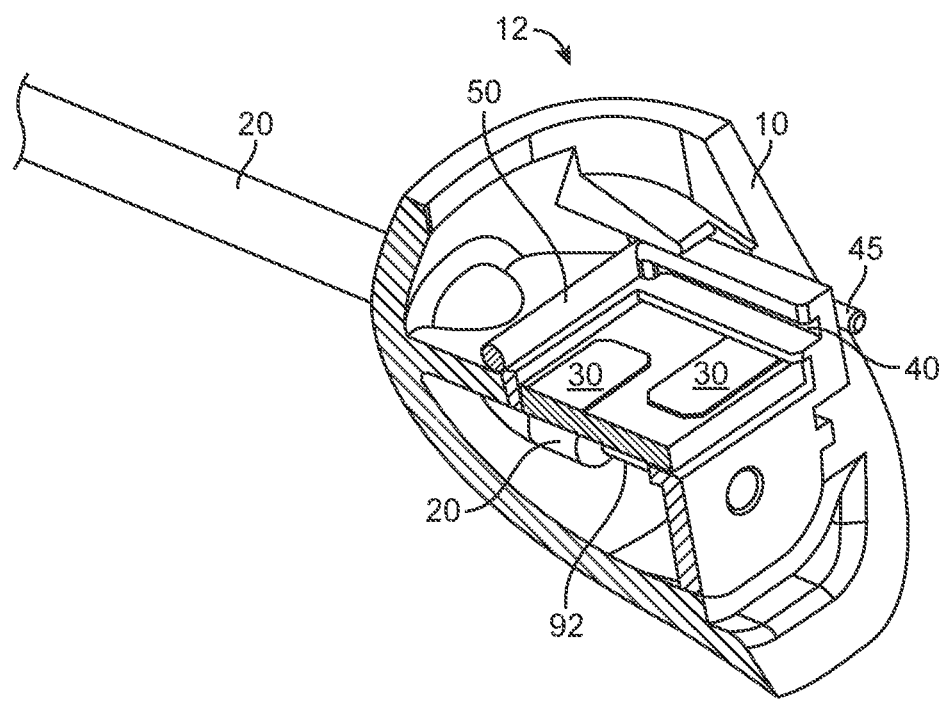
FIG. 4 is a cutaway perspective view of a lateral end of a light tip connector according to the present invention.
Figure 5:
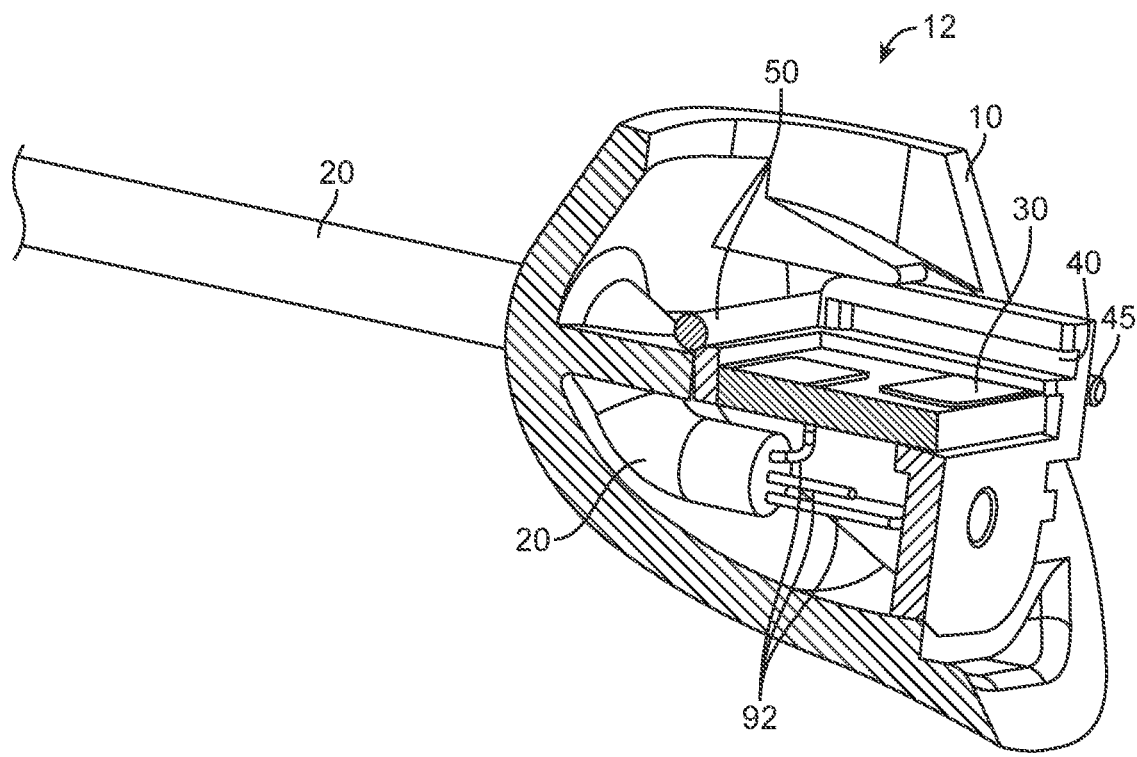
FIG. 5 is a cutaway view of a lateral end of a light tip connector according to the present invention.

FIGS. 4 and 5 are cutaway perspective views of a medial end of a light tip connector 12 according to the present invention. In FIGS. 4 and 5, LT cable 20 extends into LT housing 10. Wires 92 extend from LT cable 20 and connect LT cable 20 to LT electrodes 30. Light tip connector 12 further includes guide channel 40 and guide pins 45.

Figure 6:
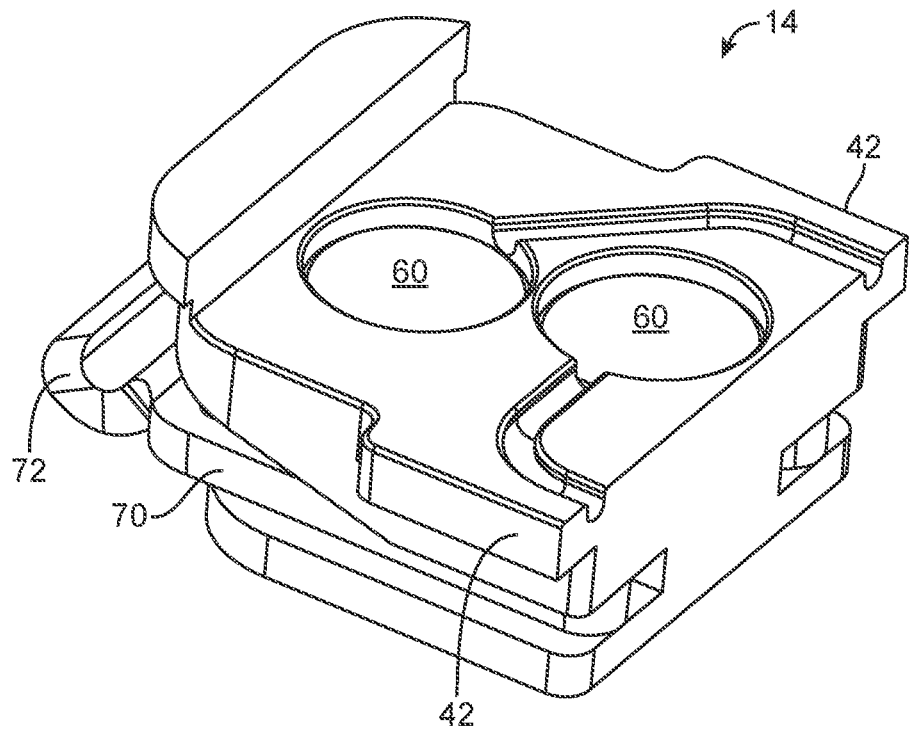
FIG. 6 is a view of an internal assembly of a BTE connector according to the present invention.

FIG. 6 is a perspective view of internal apparatus 14 of a BTE connector (not shown) according to the present invention. In FIG. 6, internal apparatus 14 includes channel guides 42, which are sized and configured to mate with guide channels 40 in light tip connector 12 when the BTE connector is connected to light tip connector 12. FIG. 6 further illustrates latch hook 72 on a medial end of latch 70.

Figure 7:
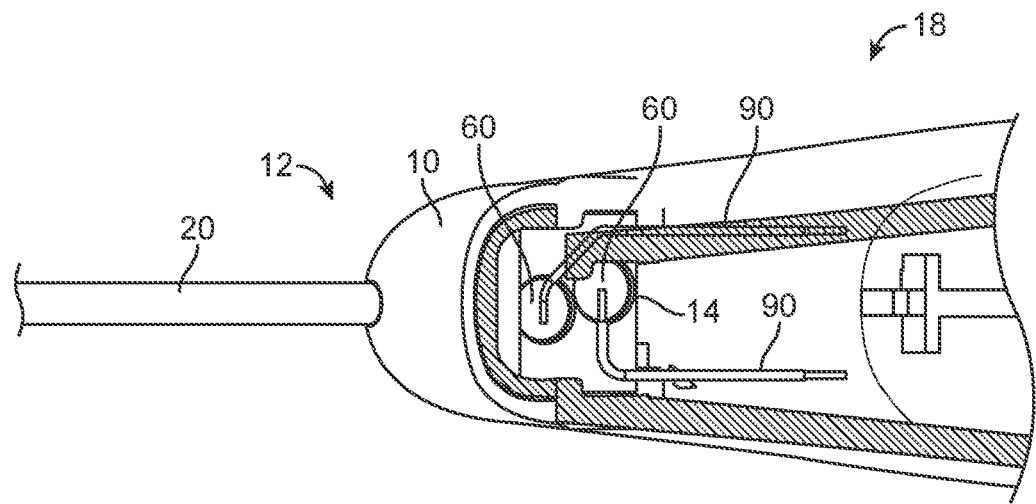
FIG. 7 is a top cut away view of a BTE connected to a light tip connector according to the present invention.

FIG. 7 is a top cut away view of a BTE 18, according to the present invention, connected to a lateral end of a light tip connector 12, according to the present invention. In FIG. 7, internal assembly 14 is illustrated positioned at a medial end of BTE 18 such that internal assembly 14 is connected to light tip connector 12 with wires 90 extending from pogo pin electrode 60 back into BTE 18 where they are connected to internal BTE circuitry (not shown). Light tip connector 12 is connected to LT cable 20 through LT housing 10.

Figure 8:
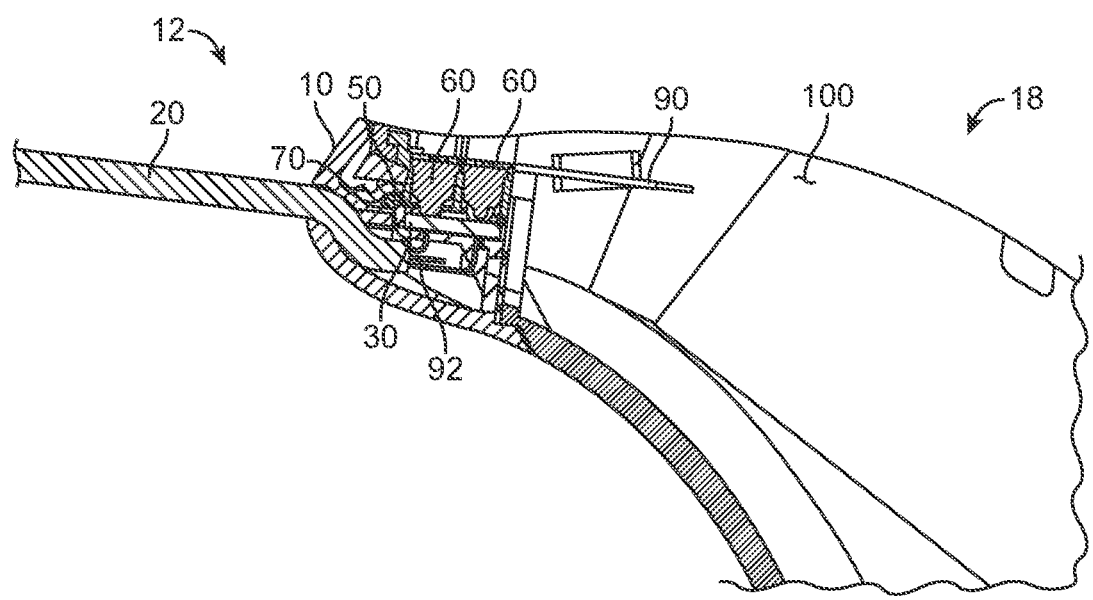
FIG. 8 is a side cut away view of a light tip connector according to the present invention, which is connected to a BTE.

FIG. 8 is a side cut away view of a light tip connector 12 according to the present invention wherein light tip connector 12 is connected to a medial end of BTE 18. In FIG. 8, LT cable 20 passes through an opening in LT housing 10 while wires 92 extend from a lateral end of LT cable 20 and are electrically connected to LT electrodes 30. When light tip connector 12 is connected to BTE 18, LT electrodes 30 are in contact with pogo pin electrodes 60, which are connected to wires 90. Wires 90 are connected to internal BTE circuitry (not shown). When light tip connector 12 is connected to BTE 18, latch 70 is positioned over locking pin 50 to hold LT connector 12 in position.

Figure 9:
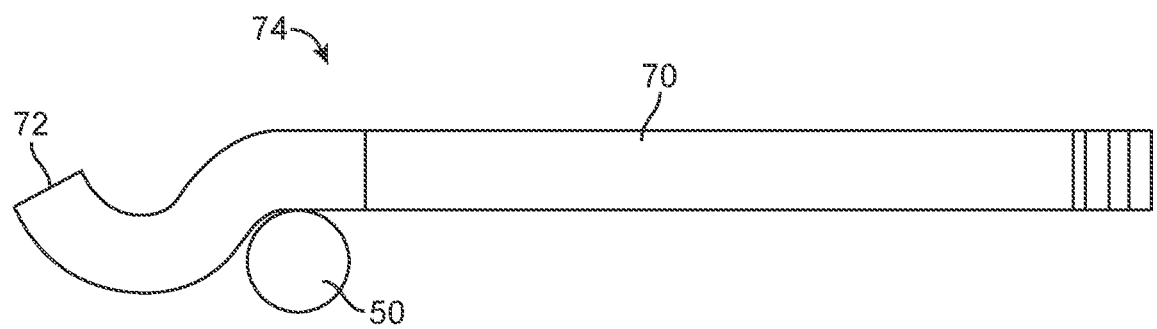
FIG. 9 is a side view of a latch and locking pin assembly according to the present invention.

FIG. 9 is a side view of a latch and locking pin assembly 74 according to the present invention. In FIG. 9, latch 70 (including latch hook 72) and locking pin 50 form locking pin assembly 74 when LT connector 12 is connected to BTE 18. Latch 70 is flexible enough to bend when latch hook 72 encounters locking pin 50 as LT connector 12 is connected to BTE 18, allowing latch hook 72 to slide up and over locking pin 50. Latch 70 is rigid enough to hold latch hook 72 in place once it is positioned on a medial side of locking pin 50. Latch 70 may be made of a spring material, allowing it to flex when required and providing rigidity when latch hook 72 is in place to form locking pin assembly 74.

Figure 10:
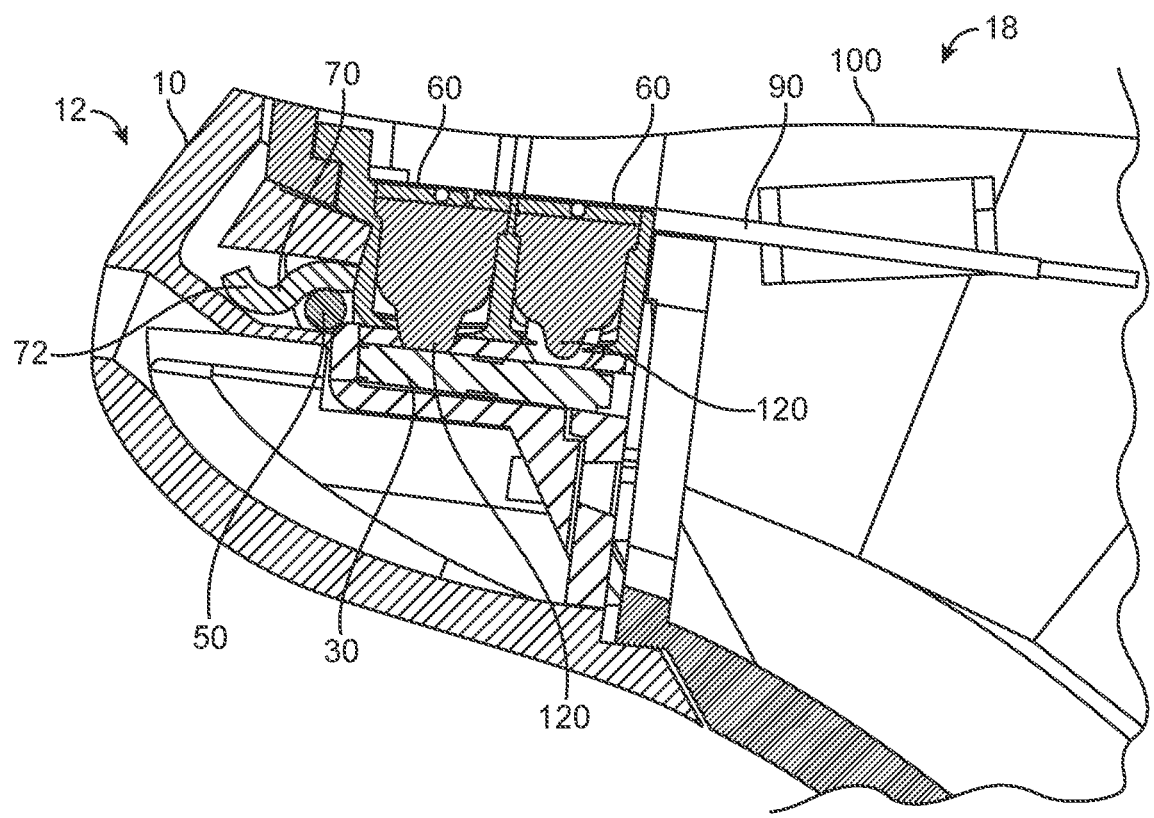
FIG. 10 is a side cut away view of a light tip connector and BTE according to the present invention.

FIG. 10 is a side cut away view of an LT connector 12 connected to a BTE 18 according to the present invention. In FIG. 10, LT housing 10 of LT connector 12 is attached to BTE housing 100 and is held in position by the interaction of latch 70 with locking pin 50 with latch hook 72 is positioned at the medial side of latch pin 50. With LT connector 12 joined to BTE 18, pogo pin electrodes 60 are in contact with LT electrode 30, such that signals from the light tip (not shown) are conveyed from LT connector 12 to BTE 18 through pogo pin electrodes 60 and wires 90. In FIG. 10, contact tips 120 of pogo pin electrodes 60 maintain electrical contact with electrodes 30.

In one embodiment of the invention, as the internal assembly 14 slides into guide channels 40, pogo pin electrodes 60 are displaced upward but springs (not shown) in the pogo pin electrodes force the pogo pin electrodes into contact with the surface of the LT connector (which includes LT electrodes 30) as latch hook 72 moves toward and contacts locking pin 50. Guide pins 45 facilitate the proper alignment of the LT housing 10 with the BTE housing 100, ensuring proper alignment of the LT connector 12 with the BTE 18 as they are connected together. As latch hook 72 moves up and over locking pin 50, the contact tips 120 of pogo pin electrodes 60 move into place against LT electrodes 30. Once LT connector 12 is attached to BTE 18, pogo pin electrodes 60 are positioned such that contact tips 120 are in electrical contact with LT electrodes 30, with contact tips 120 of pogo pin electrodes 60 pressed against LT electrodes 30 by their internal spring mechanisms to ensure good electrical contact. The present invention may be optimized to ensure retention of the connection by, for example, increasing the rigidity and/or spring constant of latch 70. In some embodiments of the invention, the force required to separate the LT connector 12 from the BTE 18 may be as high as 18 Newtons. A connector according to the present invention may be readily be adapted to incorporate more than 2 pogo pins, for example; a 4-pin or 6-pin connector.

In embodiments of the invention, system connection (both electrically and mechanically) is achieved by inserting the LT connector 12 into internal assembly 14 in BTE 18. Guide channels 40 and guide pins 45 in LT connector 12 mate with corresponding mating features in internal assembly 14 (e.g., channel guides 42). As LT connector 12 and BTE 18 come together guide channels 40 and guide pins 45 provide alignment and ensure that LT connector 12 mates properly with internal assembly 14. Latch 70 in internal assembly 14 articulates (bends) up and over locking pin 50 in LT connector 12 to secure the two assemblies together. After LT connector 12 is fully inserted, latch 70 returns to its normal position, latching LT connector 12 to internal assembly 14 and BTE 18. The material, shape, and thickness of the material used in latch 70 may be adjusted to provide optimal latching/retention force between LT connector 14 and BTE 18. In one embodiment of the invention, a flex circuit (not shown) or discreet wires 90 may be employed to connect Pogo-Pin electrodes 60 to a PCB on BTE 18.

The BTE/LT connector sub-assembly illustrated in FIGS. 1-10 is depicted as a 2-pin (2-connector) design. This connector concept can be modified to include 3 or more pins, dependent upon connector requirements. The layout of the Pogo-Pins and PCB can be reversed (if desired), by placing the Pogo-Pins in the LT connector and the corresponding PCB into the BTE sub-assembly. This connector concept can be designed to meet an IP57 rating (prevention of water and dust ingress) by sealing the BTE sub-assembly into the BTE Housing and sealing or potting the Light tip Connector Assembly.

The current design is advantageous because the arrangement of the pogo pin electrodes and the latching mechanism provide a connector that reduces the length of the overall connector, creating a more compact connector, while maintaining the connection strength and improving resistance to the ingress of water into the BTE. In addition, the use of a latch and pin mechanism removes any strain on the electrodes or electrode connection resulting from strains on the connector/BTE interface. The latch and pin assume all the strain of making, maintaining and releasing the connection, reducing or eliminating any strain on the electrical connections and increasing the life of the connector, even when the LT connector is removed from and replaced on the BTE multiple times. In this arrangement, the electrical connections are orthogonal to the latching direction and do not act as components of the latching mechanism or provide any latching function. The current design is further advantageous because it provides a hermetically sealed connection, with only wires 90 passing through the walls of BTE housing 100. All internal electronics are protected from bodily fluids and other fluids, including sweat and rain. In a further advantage, in the present invention the direction of the pogo pin actuation is at a right angle (perpendicular or orthogonal) to the locking direction of the Connector Assembly to the BTE Housing Connector Assembly. This minimizes the potential of the pogo pins to dislodge the Light tip Connector Assembly from the BTE Housing Connector Assembly.

It will be apparent to those of skill in the art that, in embodiments of the present invention, elements of the preferred embodiment may be included on components other than the components described herein. For example, internal assembly 14 may include one or more of guide pins 45, guide channels 40 or electrodes 40, with their associated mating parts being included on LT connector 14. Alternatively, in embodiments of the present invention, LT connector 12 may include one or more of channel guides 40 or pogo pin electrodes 60.

Embodiments of the present invention include a compact connector comprising a light tip connector including a light tip cable connected thereto. In this embodiment, the light tip connector may comprise: a receiving cavity including side walls and a bottom wall; guide channels formed in the side walls of the receiving cavity; a locking pin at a medial end of the guide channel; and one or more light tip electrodes positioned on a bottom wall of the receiving cavity. A compact connector according to the present invention may further comprise a BTE connector comprising: a latch adapted to engage the locking pin to hold the BTE connector in the receiving cavity when the BTE connector is attached to the light tip connector; and a plurality of pogo pin electrodes arranged to contact the light tip electrodes when the BTE connector is attached to the light tip connector. A compact connector according to the present invention may further comprise springs positioned to bias the pogo pin electrodes toward the light tip electrodes when the BTE connector is attached to the light tip connector. A compact connector according to the present invention may further comprising connection wires contacting the light tip electrodes to connect the light tip electrodes to the light tip cable. A compact connector according to the present invention may further comprise guide pins on the light tip housing, the guide pins being positioned to engage the BTE housing when the BTE connector is attached to the light tip connector. A compact connector according to the present invention further comprising wires connected to electrodes on a lateral end of the pogo pin electrodes. A compact connector according to the present invention further comprises a compact connector wherein the latch comprises a hook at a medial end thereof. A compact connector according to the present invention further comprises a compact connector wherein the latch is a spring latch.

Embodiments of the present invention include a light tip connector including a light tip cable connected thereto, wherein the light tip connector comprises: a receiving cavity including side walls and a bottom wall; guide channels formed in the side walls of the receiving cavity; a locking pin at a medial end of the guide channel; and one or more light tip electrodes positioned on a bottom wall of the receiving cavity.

Embodiments of the present invention include a BTE connector comprising: a latch adapted to engage the locking pin to hold the BTE connector in the receiving cavity when the BTE connector is attached to the light tip connector; and a plurality of pogo pin electrodes arranged to contact the light tip electrodes when the BTE connector is attached to the light tip connector.

Embodiments of the present invention include a method of connecting a BTE to a light tip, using a light tip connector, the method comprising the steps of: aligning the light tip connector to the BTE using guide pins located on either the light tip connector or the BTE; engaging channel guides located on either the BTE or the light tip connector with channels formed in either the light tip connector or the BTE; engaging a latch hook positioned on either the BTE or the light tip connector with a locking pin arranged on either the BTE or the light tip connector such that the latch hook rides up and over the locking pin as the BTE and light tip are connected; and engaging pogo pin electrodes arranged such that the direction of motion of the pogo pin electrodes is substantially orthogonal to the direction of motion of the BTE and light tip connector, wherein contact tips on the pogo pin electrodes are in electrical contact with electrodes when the BTE is connected to the light tip connector.

In embodiments of the invention, the light tip (also referred to as an ear tip) may include a detachable outer shell, allowing the outer shell to be replaced if it is no longer acceptable to the user (e.g. it tears or becomes worn). Replaceable light tips are also advantageous because it allows the manufacturer to ship more than one outer shell and the health care professional to select the shell which is the best fit (e.g., most comfortable) for the user. Alternatively, a replaceable light tip is also advantageous because it enables the health care professional to swap out emitters and cables while keeping a light tip which is the best fit for the user (e.g., where an emitter has failed or a cable is too long or too short). In embodiments of the invention, ear tip 222 may comprise an emitter 290 attached to one end of LT cable 20, along with a light tip shell 505, which is detachable from LT cable 20, allowing either LT cable 20 or ear tip shell 505 to be replaced.

Figure 11:
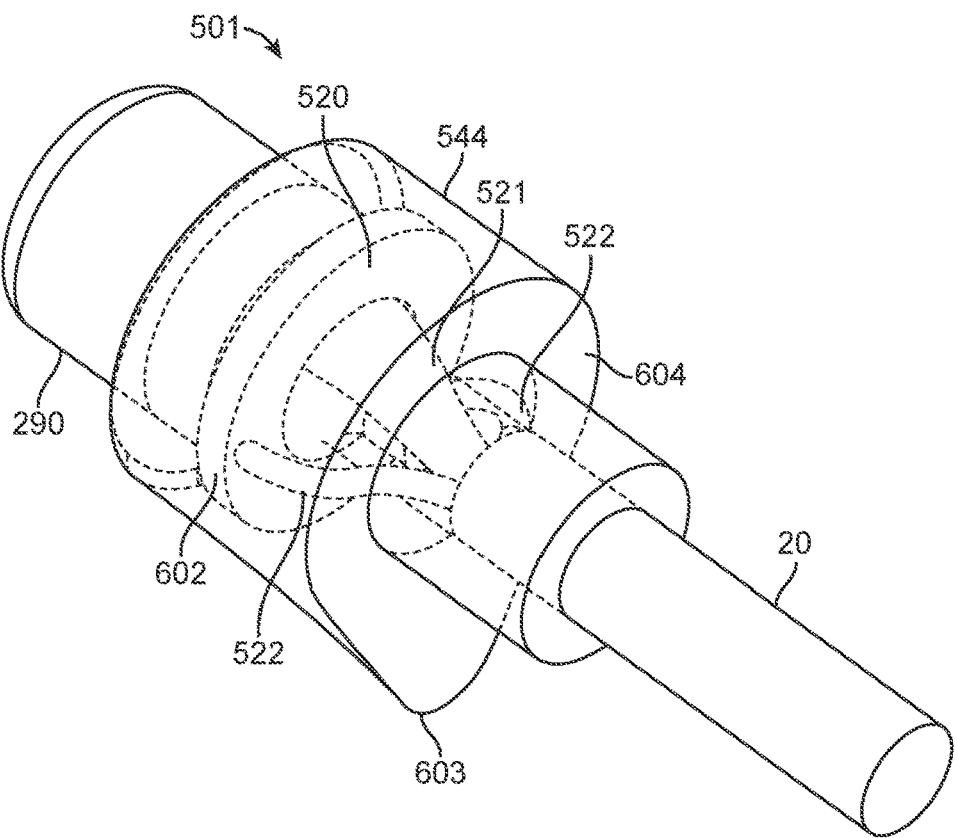
FIG. 11 is a perspective view of a medial end of an LT cable according to the present invention.

FIG. 11 is a perspective view of the light tip (medial) end of LT cable 20. In FIG. 11, light tip shell 505 is not shown but would, if shown, be connected to LT cable 20. In embodiments of the invention, LT cable 20 may include a cartridge assembly 501 at the light tip end of LT cable 20. Cartridge assembly 501 may comprising an emitter 290, which may be an infrared laser, and may further include a load bearing strand 521, which may be made of Kevlar. Load bearing strand 521 may be bonded to emitter housing 520 to prevent LT cable 20 from pulling away from cartridge assembly 501. In the embodiment of FIG. 11, cable conductors 522 from LT cable 20 may be soldered to the anode (not shown) and cathode (not shown) of emitter 290. Retention features 544, including lobe 603 and lateral face 604, may be over-molded onto emitter 290 to form cartridge assembly 501. In the embodiment, illustrated in FIG. 11, emitter 290 may further include flange 602.

Figure 12:
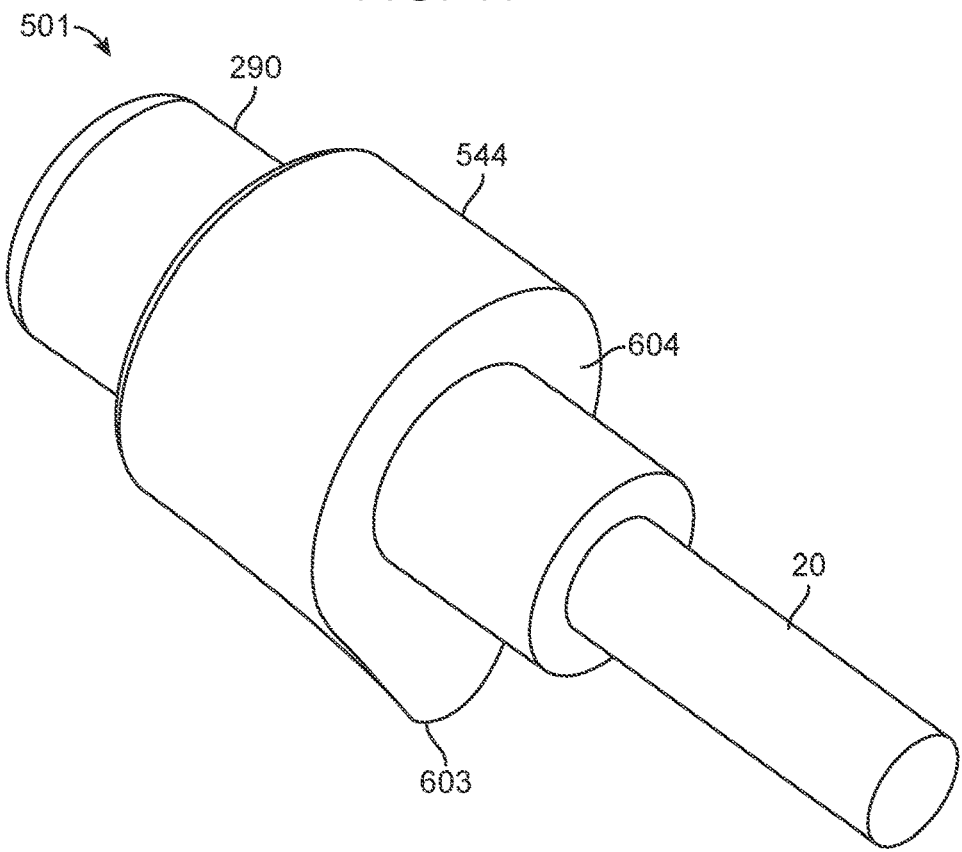
FIG. 12 is an alternative view of a cartridge assembly according to the present invention.

FIG. 12 is an alternative view of cartridge assembly 501. In FIG. 12, the hidden features shown in FIG. 11 are no longer visible. In FIG. 12, LT cable 20 passes through retention features 544 and is connected to emitter 290 through cable connectors 522 and load bearing strand 521 (not shown). Retention feature 544 may include lobe 603 and lateral face 604.

Figure 13:
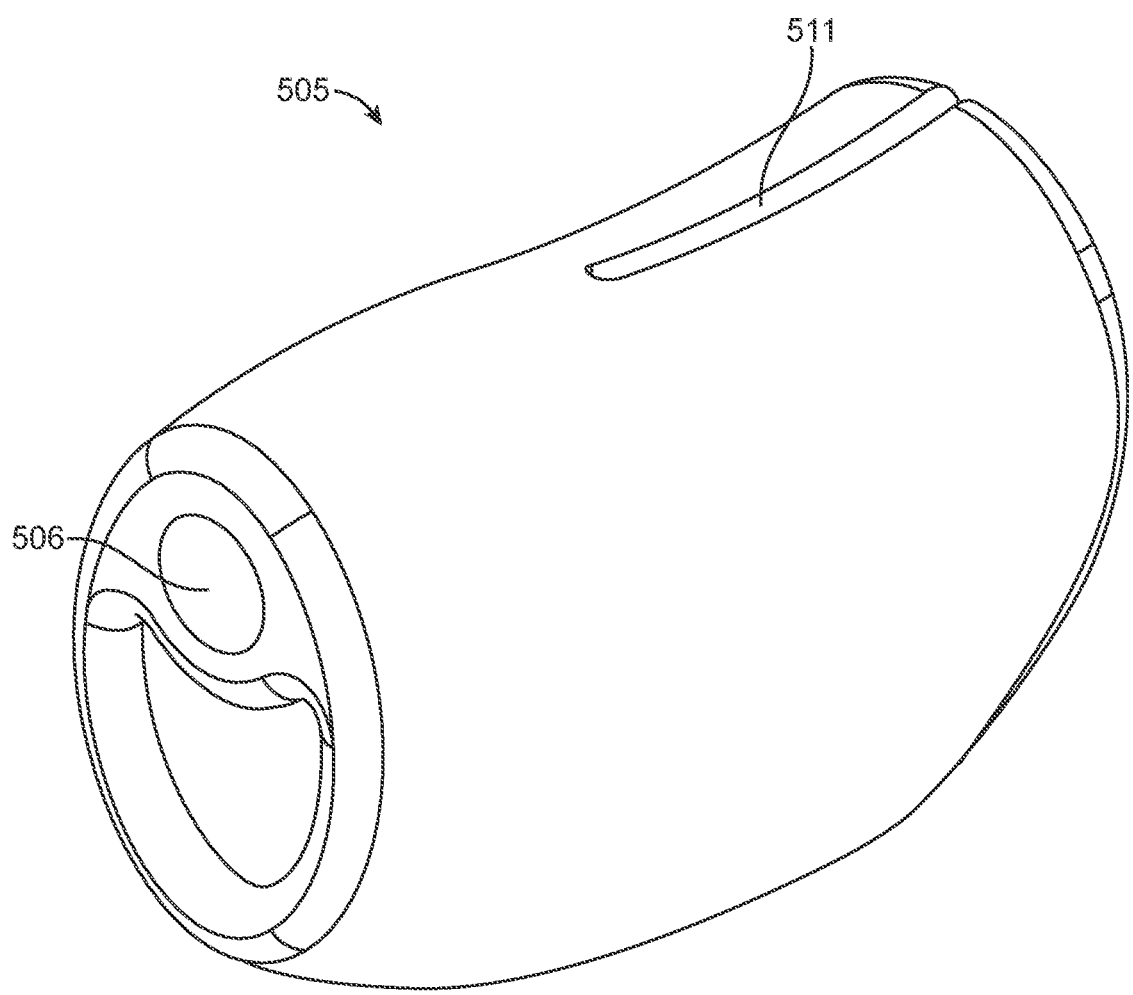
FIG. 13 is an illustration of a replaceable light tip shell according to the present invention.

FIG. 13 is an illustration of a replaceable light tip shell 505 according to the present invention. In embodiments of the invention, light tip shell 505 may be combined with cartridge assembly 501 (not shown) to complete light tip 222 (not shown) at the light tip end of LT cable 20 (not shown). Light tip shell 505 is adapted to be removeably connected to cartridge assembly501 such that LT cable 20 may be combined with different light tip shells 505, allowing light tip shells 505 and/or LT cables 20 to be selected to accommodate the needs of individual users. In embodiments of the invention, the combined light tip shell 505 and cartridge assembly 501 form light tip 222. In embodiments of the invention, light tip shell 505 may include cylindrical bore 506 and superior slot 511.

In attaching light tip shell 505 to cartridge assembly 501, three characteristics of the combined device are extremely important. In particular, the strength of the connection is important to prevent light tip shell 505 from separating from cartridge assembly 501 when a user takes light tip shell 505 out of their ear by, for example, grabbing LT cable 20 and pulling. In addition, because each light tip shell is customized to ensure the proper placement and alignment of emitter 290 when light tip 222 is in a user's ear, it is very important to ensure that, when light tip shell 505 is combined with cartridge assembly 501, including emitter 290, the positioning and alignment of emitter 290 is correct. Finally, it is important that the attachment and removal of light tip shell 505 from cartridge assembly 501 be simple and easy to accomplish.

Figure 14:
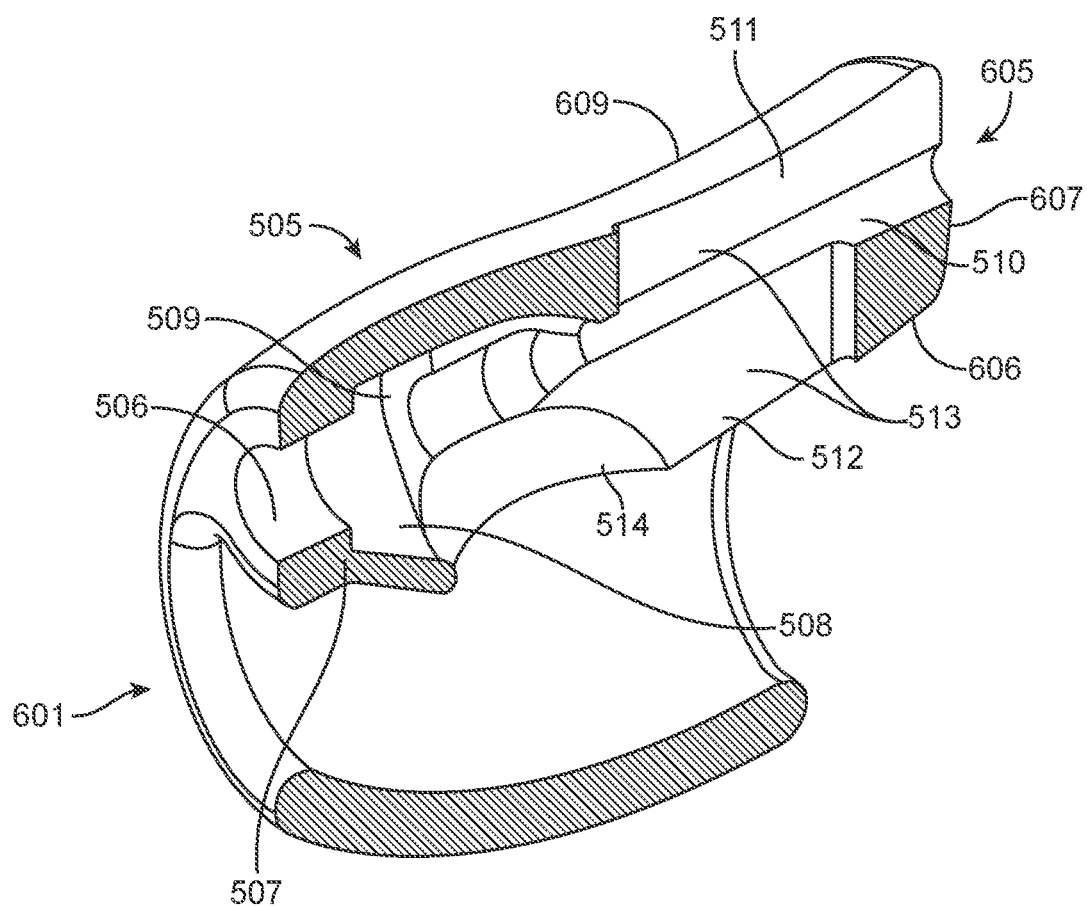
FIG. 14 is a cut away view of a replaceable light tip shell according to the present invention.

FIG. 14 is a cut away view of a light tip shell 505 according to the present invention. Light tip shell 505 has features that are adapted to retain cartridge assembly 501 in light tip shell 505 and to align emitter 290 when it is properly positioned in light tip shell 505. At medial end 601 of light tip shell 505, a cylindrical bore 506 provides angular alignment of emitter 290 by mating with the cylindrical outer surface of the emitter housing 520 when emitter 290 is positioned in light tip shell 505. At medial end 601 of light tip shell 505, a face 507 provides a depth stop for emitter 290 by interfacing with flange 602 on emitter 290 when emitter 290 is positioned in light tip shell 505. Light tip shell 505 has a lobe shaped opening 508 to interface with lobe 603 on cartridge assembly 501 to provide rotational keying between cartridge assembly 501 and light tip shell 505 when cartridge assembly 501 is positioned in light tip shell 505. Back stop 509 in light tip shell 505 contacts lateral face 604 of retention feature 544 to retain cartridge assembly 501 in light tip shell 505 when cartridge assembly 501 is positioned in light tip shell 505. Circular cross section cable groove 510 retains and routes LT cable 20 when cartridge assembly 501 is positioned in light tip shell 505. In one embodiment of the invention, inferior slot 512 starts approximately 2 to 4 mm from lateral end 605 of light tip shell 505 and ends at tear drop feature 514. Tear drop feature 514 extends from inferior slot 512 to backstop 509. In embodiments of the invention, light tip shell 505 may include continuous slot 513, inferior side 606 of light tip shell spine 607, light tip shell spine 607, and superior side 609.

Figure 15:
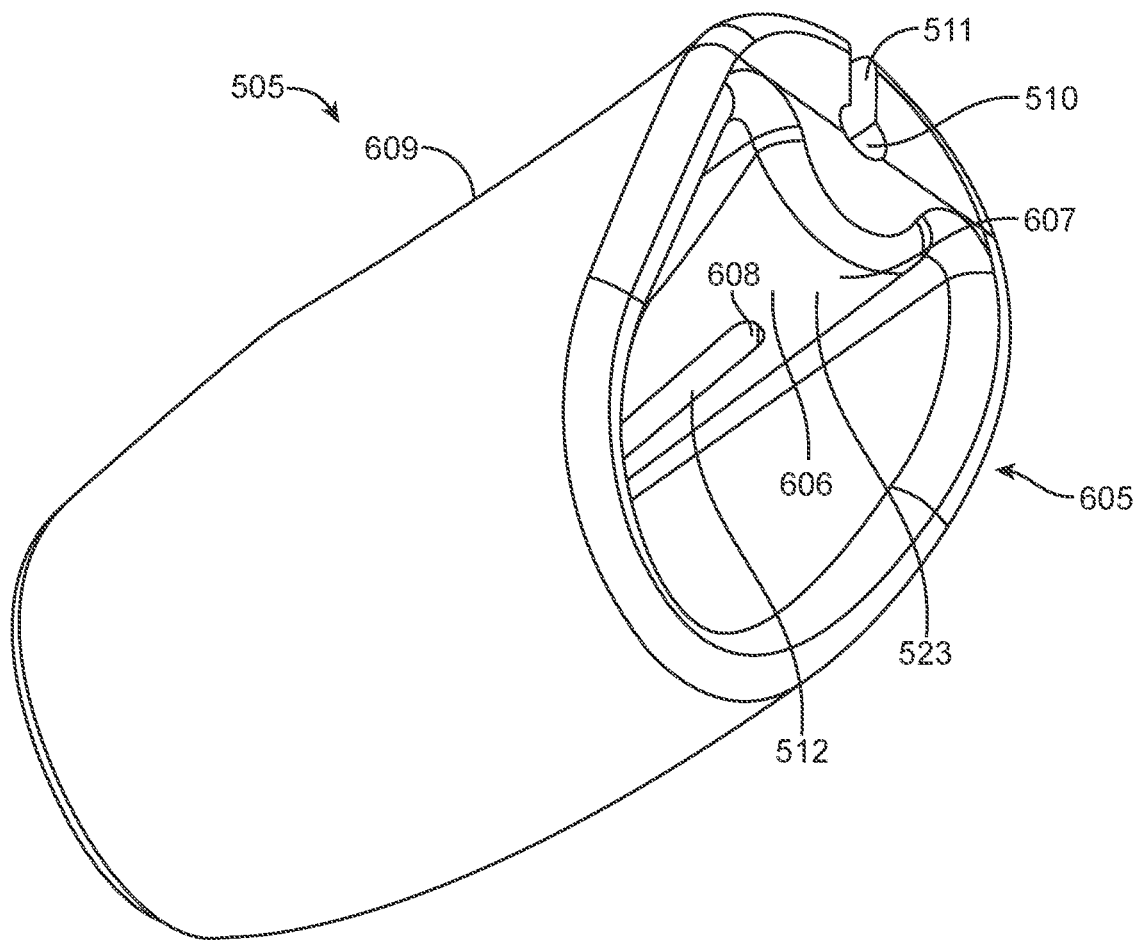
FIG. 15 is an end perspective view of a replaceable light tip shell according to the present invention.
Figure 16:
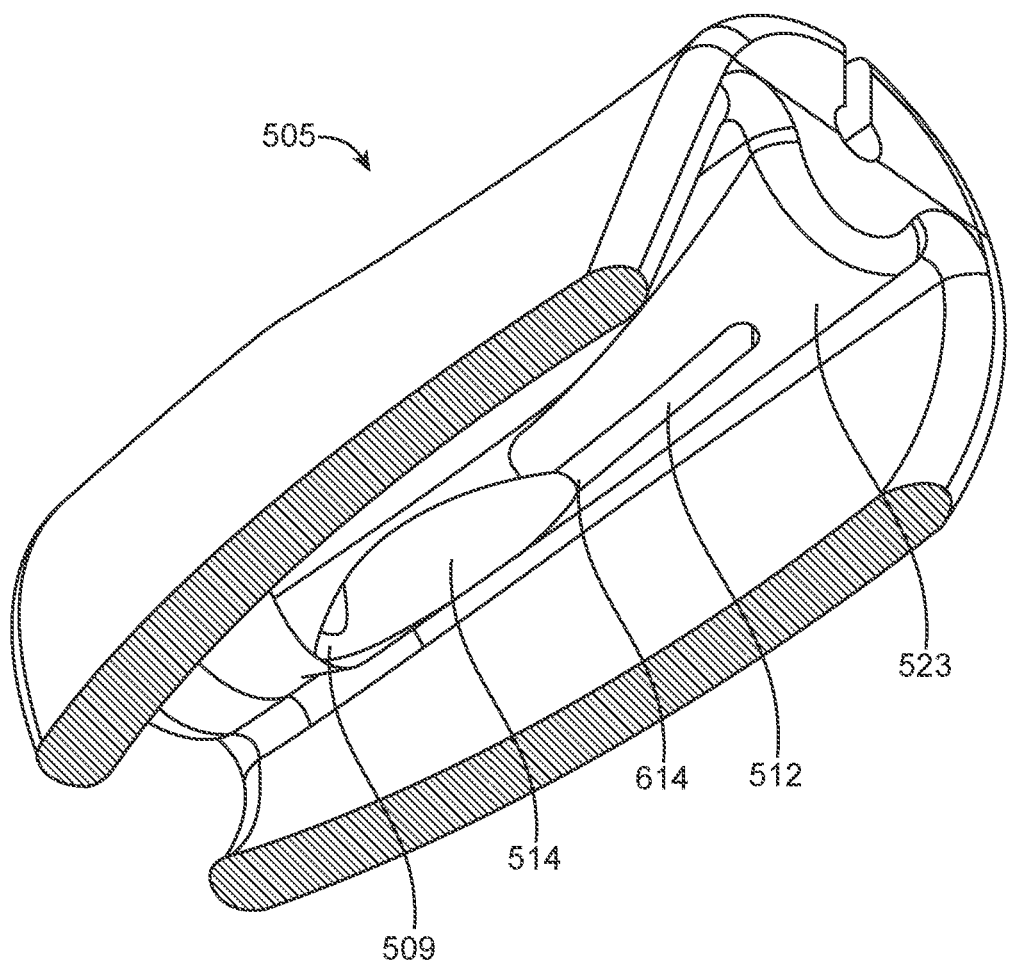
FIG. 16 is a cut away view of a replaceable light tip shell according to the present invention.

FIG. 15 illustrates a light tip shell 505 according to the present invention. FIG. 16 is a cutaway view of a light tip shell 505 according to the present invention. Light tip shell 505 has features that allow easy insertion of cartridge assembly 501 into light tip shell 505. Superior slot 511 starts at lateral end 605 of light tip shell 505 and ends near the middle of light tip shell 505. Superior slot 511 extends from the superior side 609 of light tip shell 505 down into cable groove 510. In embodiments of the invention, the 2 to 4 millimeters of solid material between the lateral end 608 of inferior slot 512 and lateral end 605 of light tip shell 505 forms a cable retention feature 523. Inferior slot 512 extends from inferior side 606 of the spine 607 of light tip shell 505 up to cable groove 510. Superior slot 511 and inferior slot 512 overlap to provide an approximately 5 mm long continuous slot 513 through light tip shell spine 607. The embodiments illustrated in FIGS. 15 and 16 further include: teardrop feature 514, medial end 614 of inferior slot 512 and back stop 509.

Figure 17:
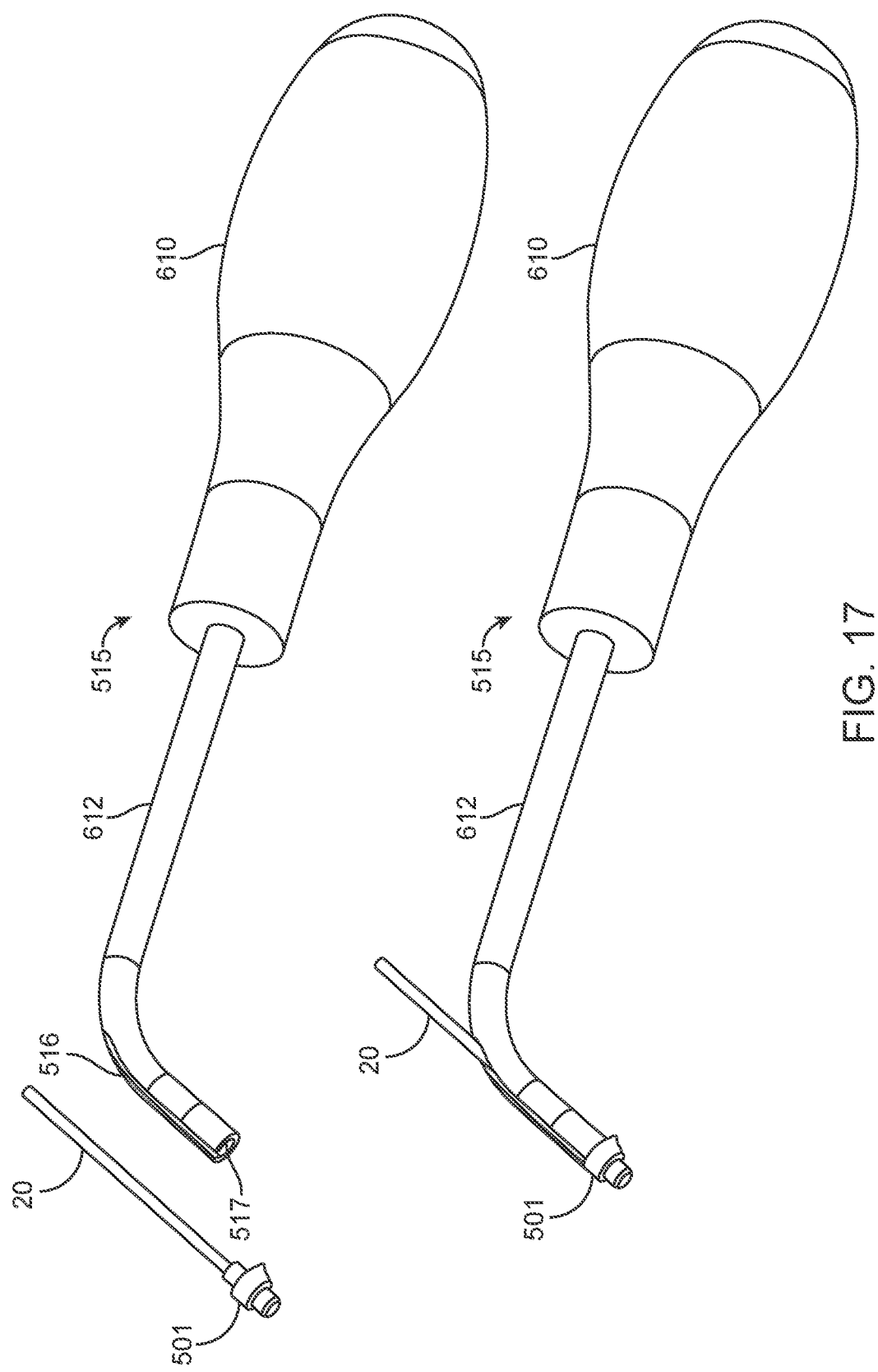
FIG. 17 is an illustration of an insertion and removal tool according to the present invention.

FIG. 17 is an illustration of an insertion and removal tool 515 according to the present invention. In FIG. 17, insertion and removal tool 515 includes handle 610, and an extension 612. Extension 612 includes tool groove 516 and counterbore feature 517. In FIG. 17, LT cable 20, including cartridge assembly 501 is shown adjacent to and positioned in tool groove 516.

Figure 18:
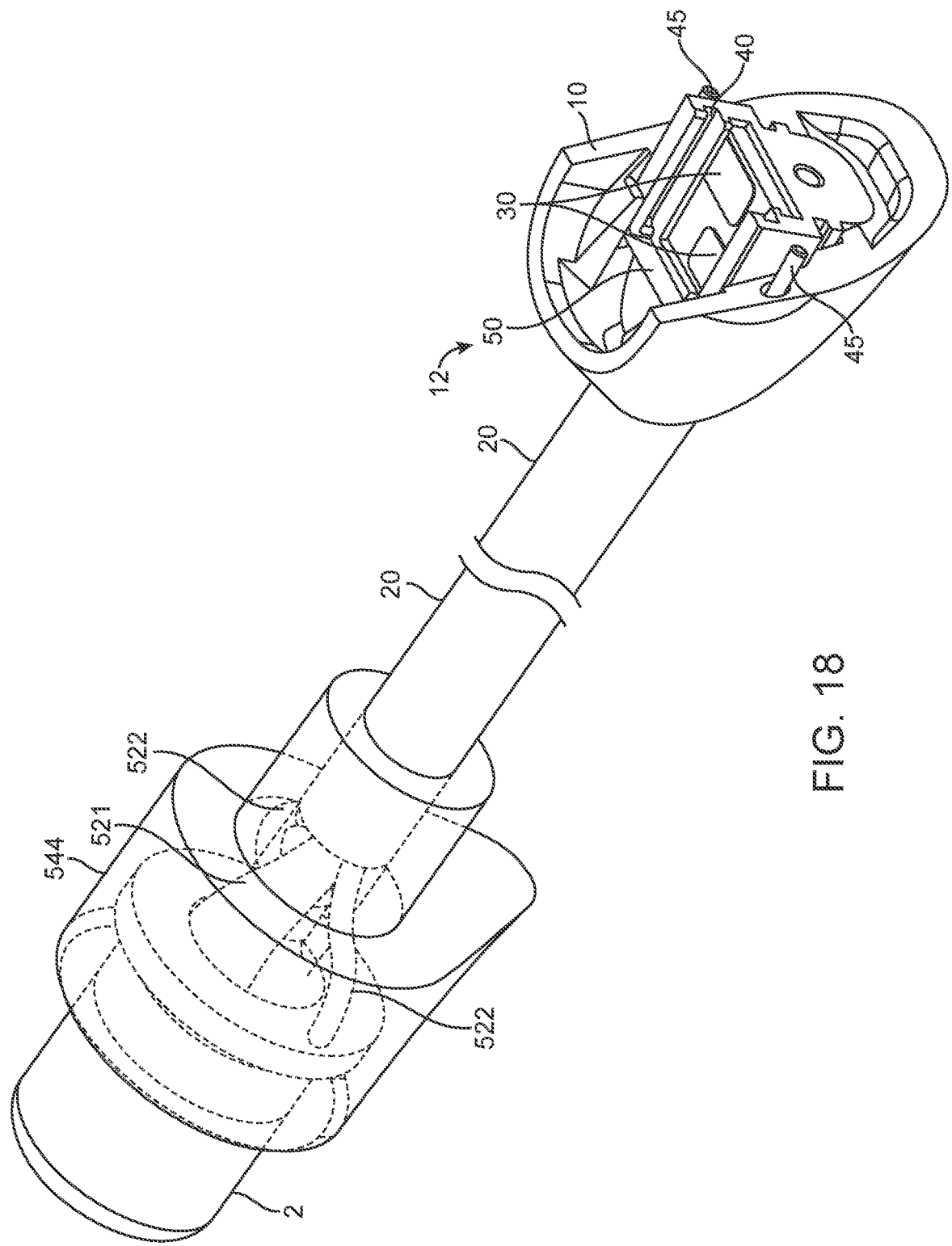
FIG. 18 is an illustration of an LT cable including a cartridge assembly and a light tip connector according to the present invention.

FIG. 18 is an illustration of an LT cable 20 according to the present invention including a cartridge assembly 501 at a first end and a light tip connector 12 at a second end.

In operation, the replaceable light tip shell 505 illustrated in FIGS. 11-16 is made of a compressible material. Compressing light tip shell 505 in the lateral—medial direction widens continuous slot 513 into an ellipse or oval similar to the shape of a "coin purse". Cartridge assembly 501 may then be inserted into light tip shell 505 through widened continuous slot 513. Medial end 614 of inferior slot 512 extends into tear drop feature 514. As cartridge assembly 501 is inserted into tear drop feature 514, inferior slot 512 expands in the anterior and posterior directions. As cartridge assembly 501, including emitter 290, is further inserted, emitter 290 enters cylindrical bore 506 and cartridge assembly 501 is moved into contact with step 507, light tip shell 505 collapses in the anterior and posterior directions, allowing the back stop 509 to contact lateral face 604 of retention feature 544. Once emitter 290 is properly positioned in cylindrical bore 506, LT cable 20 will be positioned in the inferior slot 512 and superior slot 511 and may be pulled into cable groove 510. Inferior slot 512 and superior slot 511 expand to allow LT cable 20 through, but return to their normal width once LT cable 20 is in cable groove 510, thus securing LT cable 20 in cable groove 510. With cartridge assembly 501 properly positioned, cable retention feature 523 at the lateral end of inferior slot 512 prevents LT cable 20 from being pulled out in the inferior direction when, for example, a user (e.g., a patient) pulls on LT cable 20 to remove light tip 222 from their ear canal.

In one embodiment of the invention, an insertion-removal tool 515 is used to aid the insertion and removal of cartridge assembly 501 into light tip shell 505. Tool 515 has a tool groove 516 and counter-bored feature 517 allowing cartridge assembly 501 to nest in tool 515 before tool 515 is used to insert cartridge assembly 501 and LT cable 20 into light tip shell 505. A light tip shell 505 and cartridge assembly 501 according to the present invention may have an interference fit between tool groove 516 and an outside diameter of LT cable 20 allowing tool groove 516 to grip LT cable 20 during insertion and removal.

In embodiments of the invention, a two-step process may be used to insert cartridge assembly 501 into light tip shell 505 using insertion-removal tool 515. Step One: with cartridge assembly 501 seated in tool groove 516, the tool-cartridge combination is used to aid insertion of cartridge assembly 501 through continuous slot 513. Cartridge assembly 501 may then be removed from tool groove 516, leaving cartridge assembly 501, including emitter 290, on the inferior side of continuous slot 512 and LT cable 20 extending from the superior side of continuous slot 513 to cartridge assembly 501. Step Two: cartridge assembly 501 is reinserted into tool groove 516. The tool-cartridge combination may then be used to aid insertion of cartridge assembly 501 through tear-drop feature 514 from the inferior side of tear drop feature 514. In embodiments of the invention, cartridge assembly 501 may be removed from a light tip shell 505 by reversing the preceding steps.

Figure 19:
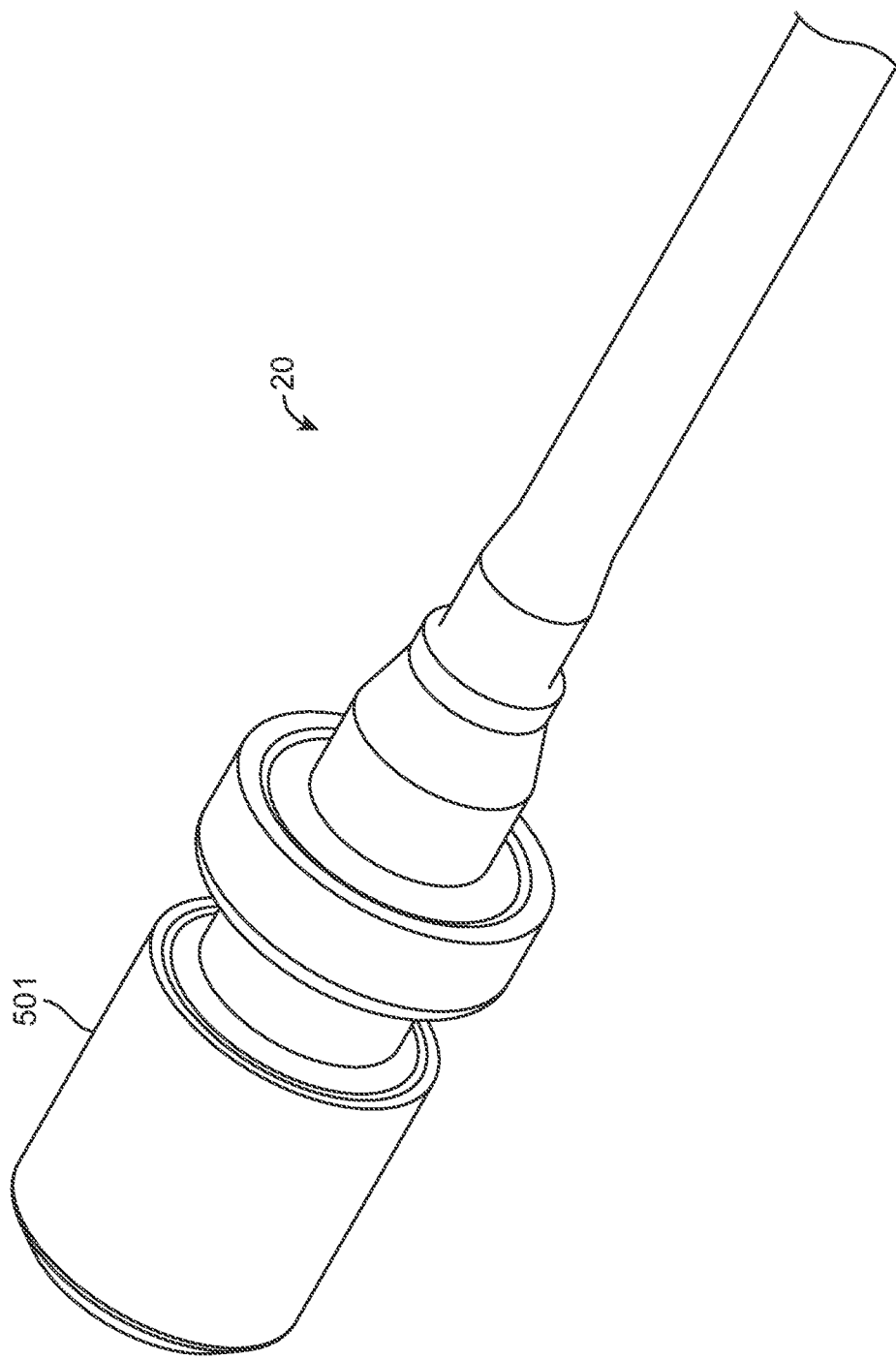
FIG. 19 is a perspective view of the medial end of an LT cable including a cartridge assembly according to one embodiment of the present invention.
Figure 20:
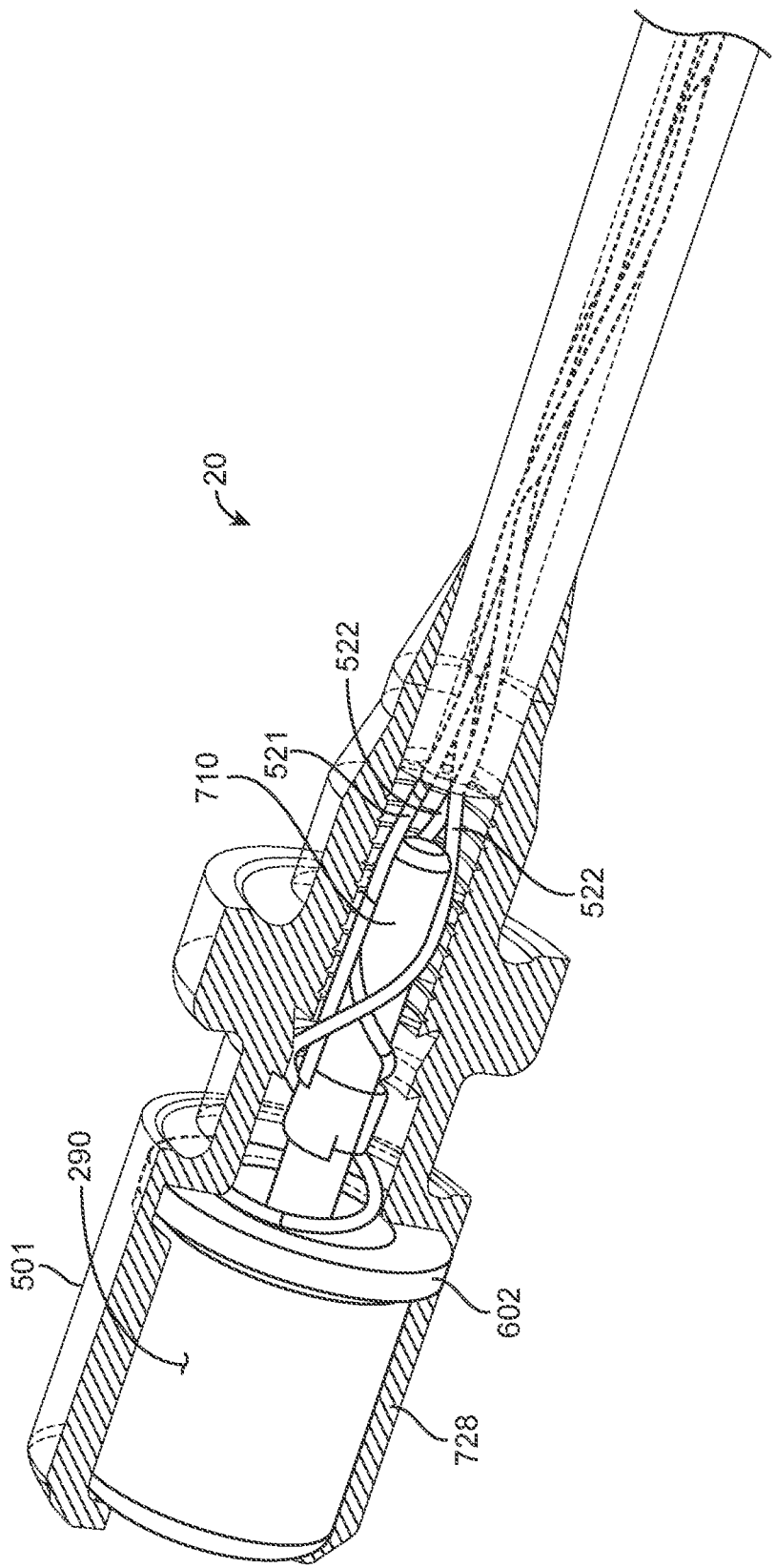
FIG. 20 is a perspective view of the medial end of an LT cable according to one embodiment of the present invention including a cartridge assembly with a portion of a cartridge assembly jacket cut away to show an emitter in the cartridge assembly jacket.

FIG. 19 is a perspective view of the medial end of LT cable 20 including a cartridge assembly 501 according to one embodiment of the present invention. FIG. 20 is a further perspective view of the medial end of LT cable 20 according to one embodiment of the present invention including a cartridge assembly 501 with a portion of cartridge assembly jacket 728 cut away to show emitter 290, load bearing strand 521 and cable connectors 522. Emitter 290 includes flange 602 and emitter post 710.

Figure 21:
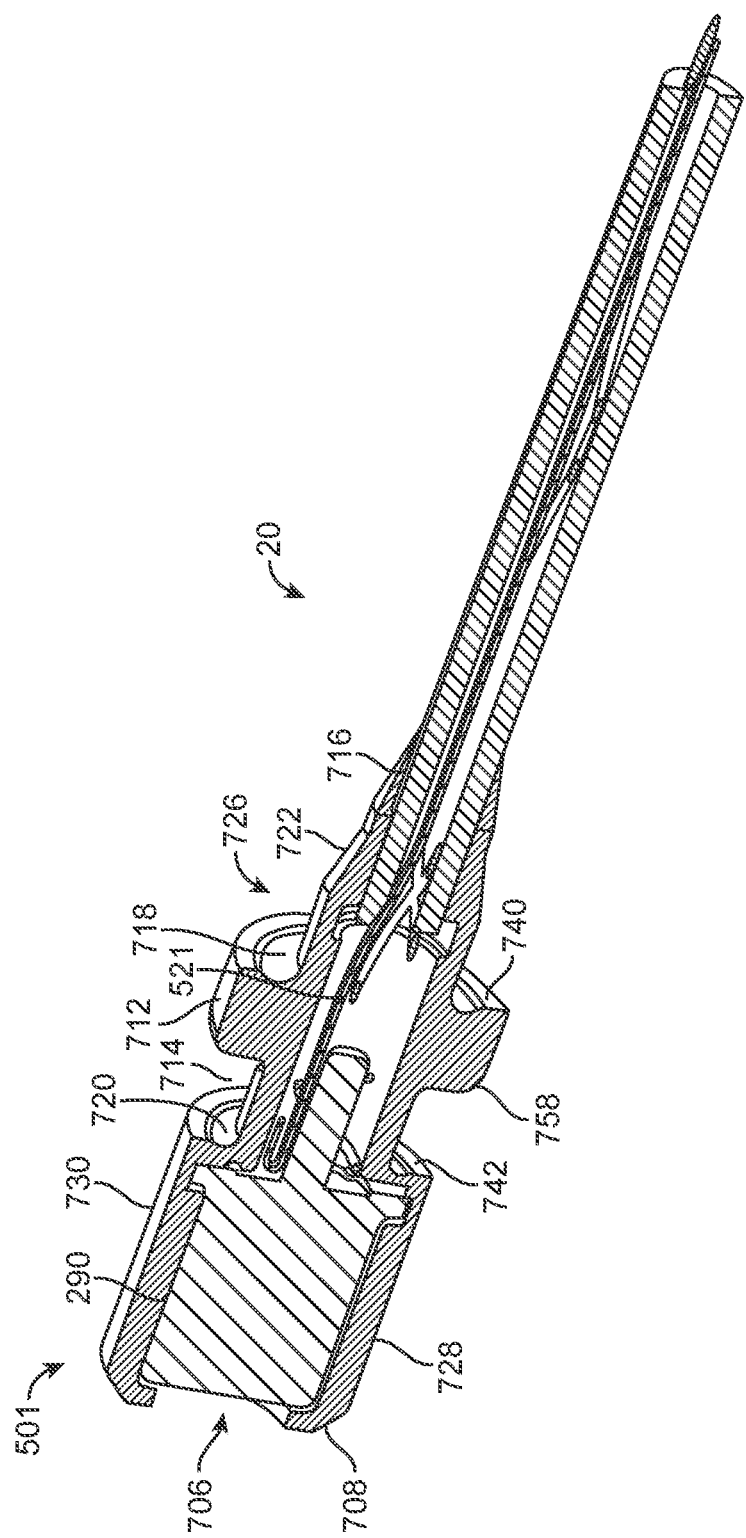
FIG. 21 is a cut away perspective view of a cartridge assembly at a medial end of an LT cable according to one embodiment of the present invention.

FIG. 21 is a cut away perspective view of a cartridge assembly 501 positioned on a medial end of a LT cable 20 according to one embodiment of the present invention. In the embodiment of FIG. 21, cartridge assembly 501 may include cartridge assembly jacket 728 and emitter 290. Cartridge assembly 501 may further include a number of retention features, including emitter retention ring 730 and cartridge assembly retention ring 712. Emitter retention ring 730 may further include medial jacket catch ring 742 and medial undercut 720. Cartridge assembly retention ring 712 may further include lateral jacket catch ring 740 and lateral undercut 718. Cartridge assembly 501 may further include retention features including medial retention groove 714 and lateral retention groove 726. Cartridge assembly 501 may further include insertion features including lead bevel 708 and lateral bevel 758. Cartridge assembly 501 may further include additional features such as emitter opening 706, lateral taper 722, load bearing strand 521, and lateral ramp 716.

Figure 21A:
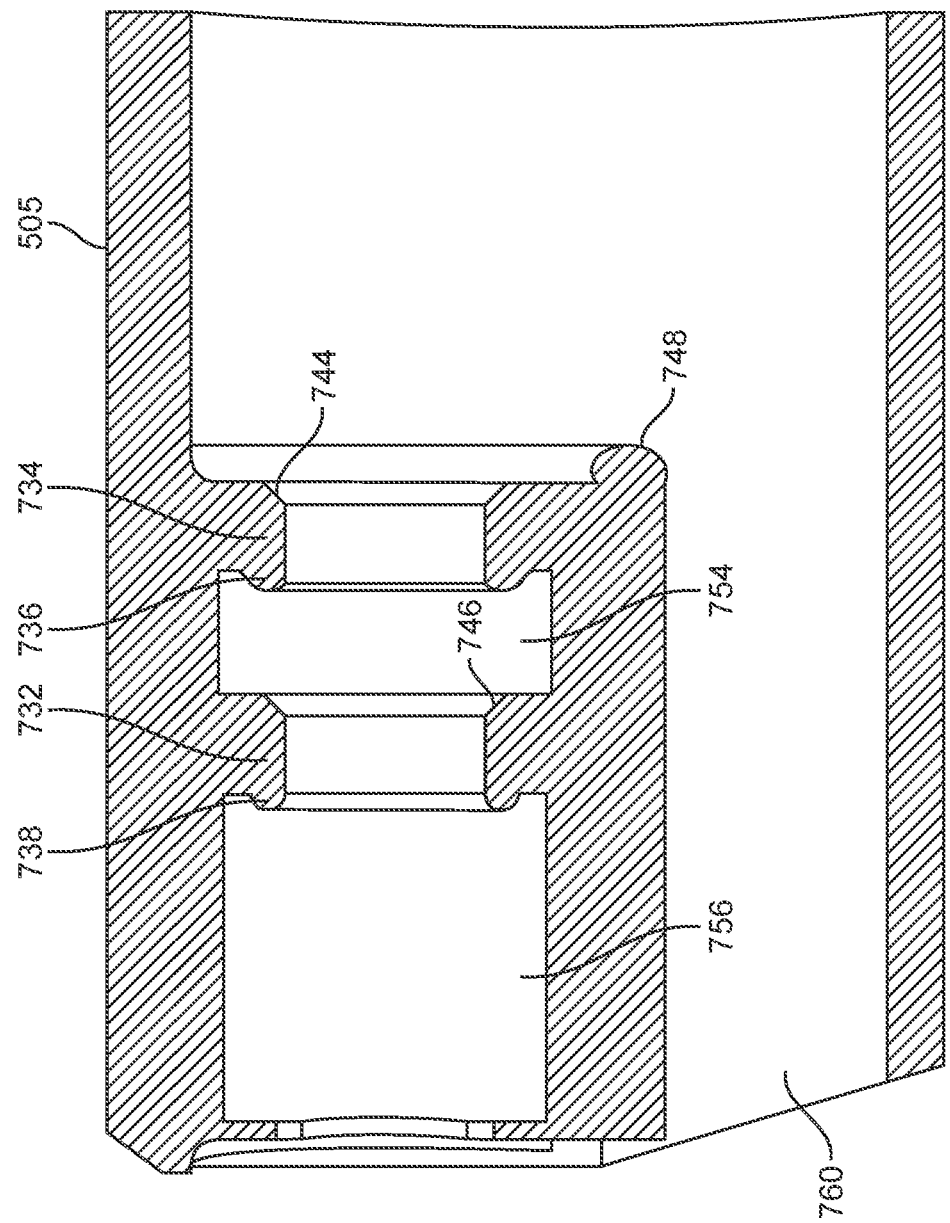
FIG. 21A is a cutaway side view of a replaceable light tip shell according to one embodiment of the present invention.
Figure 21B:
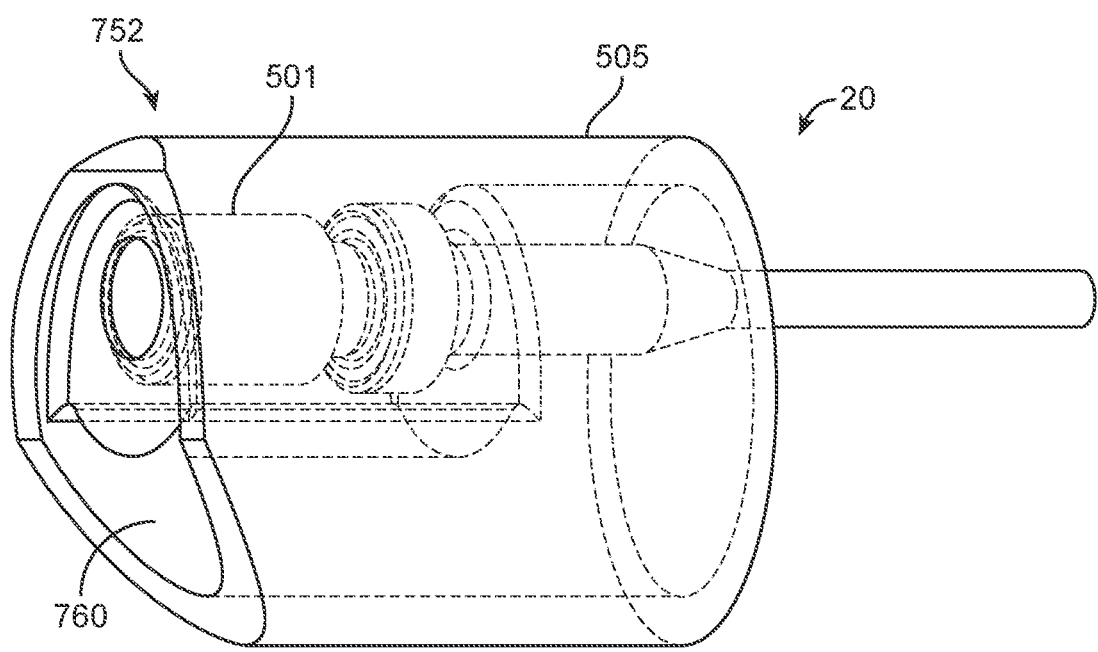
FIG. 21B is a side perspective view of a light tip assembly according to the present invention showing s cartridge assembly positioned in a replaceable light tip shell at a medial end of an LT cable.

FIG. 21A is a cutaway side view of replaceable light tip shell 505 according to one embodiment of the present invention. In FIG. 21A, light tip shell 505 may include retention elements including medial shell catch ring 738, medial shell retention ring 732, lateral shell catch ring 736, and lateral shell retention ring 734. Light tip shell 505 may further include retention elements including emitter cavity 756 and shell lateral retention groove 754. Light tip shell 505 may further include retention elements including stabilizing ring 748. Light tip shell 505 may further include insertion elements including lateral shell insertion bevel 744 and medial shell insertion bevel 746. Light tip shell 505 may further include acoustic vent 760. FIG. 21B is a side perspective view of light tip assembly 752 showing cartridge assembly 501 positioned in replaceable light tip shell 505 at a medial end of LT cable 20. In FIG. 21B, light tip assembly 505 may include acoustic vent 760.

Figure 22:
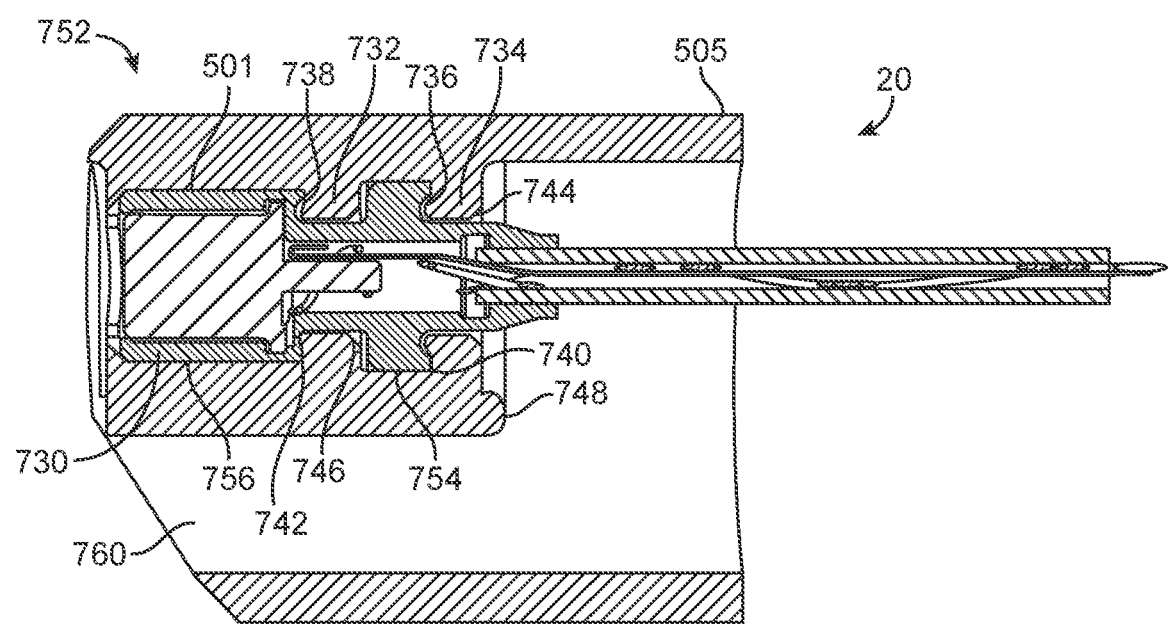
FIG. 22 is a cut away side view of the medial end of an LT cable including a cartridge assembly and light tip shell according to one embodiment of the invention.
Figure 23:
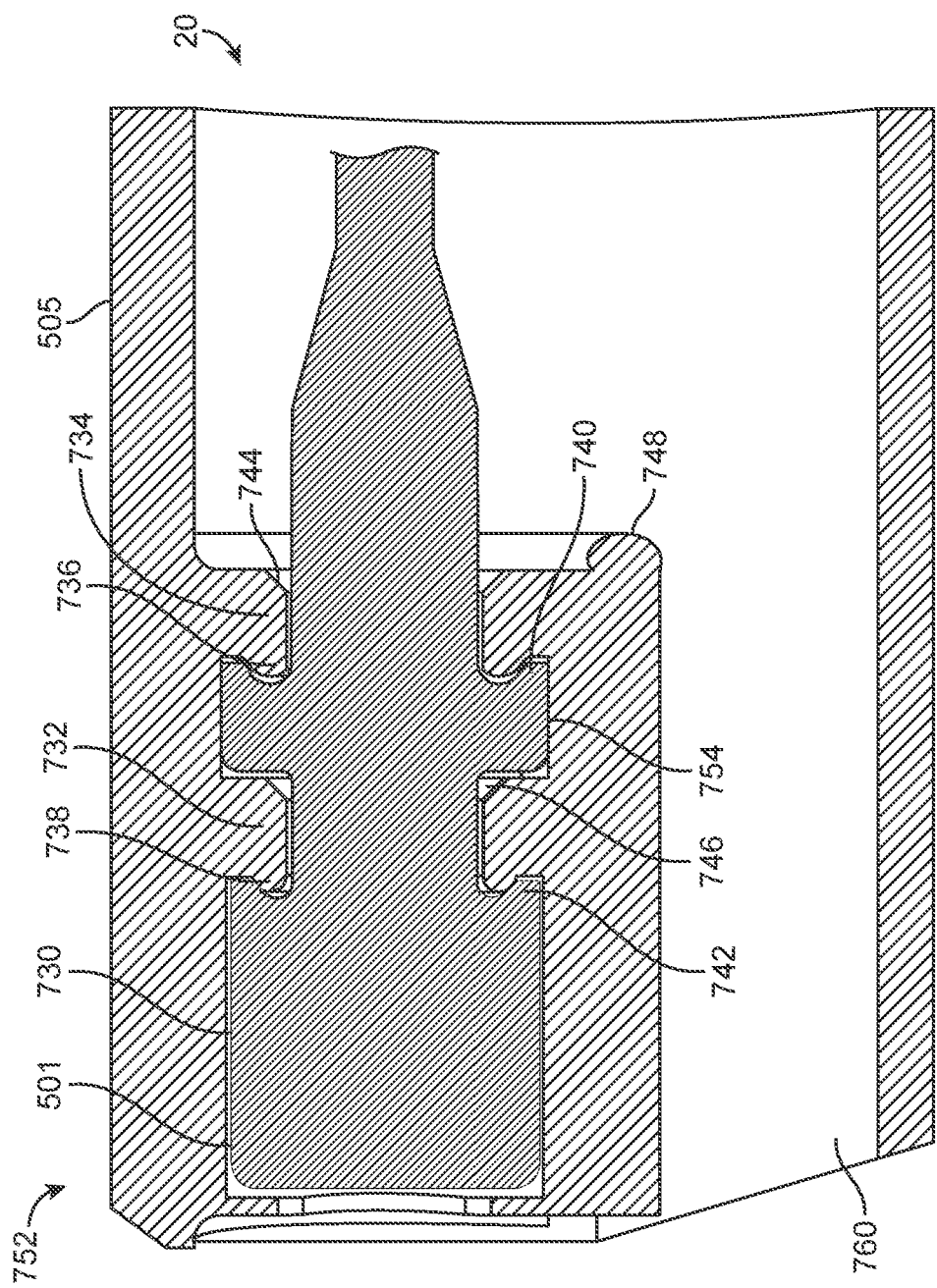
FIG. 23 is a cut away side view of a cartridge assembly and light tip shell according to one embodiment of the invention.

FIGS. 22 and 23 are a cut away side views of light tip assembly 752 at a medial end of LT cable 20. In the embodiment of FIGS. 22 and 23, light tip assembly 752 includes cartridge assembly 501 and replaceable light tip shell 505. In the embodiment illustrated in FIGS. 22 and 23, cartridge assembly 501 is positioned in light tip shell 505. In the embodiment of FIGS. 22 and 23, cartridge assembly 501 includes the features described above with respect to FIG. 21. In the embodiments of FIGS. 22 and 23, light tip shell 505 includes the features described above with respect to FIG. 21A. In the embodiments of FIGS. 22 and 23, light tip shell 505 includes a number of retention features including medial shell catch ring 738, medial shell retention ring 732, lateral shell catch ring 736, lateral shell retention ring 734, and stabilizer ring 748. Light tip shell 505 may further include insertion features such as medial shell insertion bevel 746 and lateral shell insertion bevel 744. The embodiments of the invention illustrated in FIGS. 22 and 23 further include emitter retention ring 730, acoustic vent 760, shell lateral retention groove 754, lateral jacket catch ring 740, medial jacked catch ring 742, and emitter cavity 756.

Figure 24A:
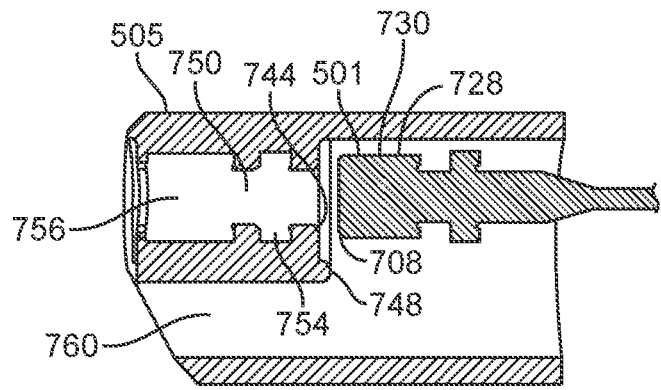
FIGS. 24A-24E are side cut away views of the cartridge assembly and light tip shell showing the sequence of insertion steps resulting in the insertion of the cartridge assembly into the light tip shell.
Figure 24B:
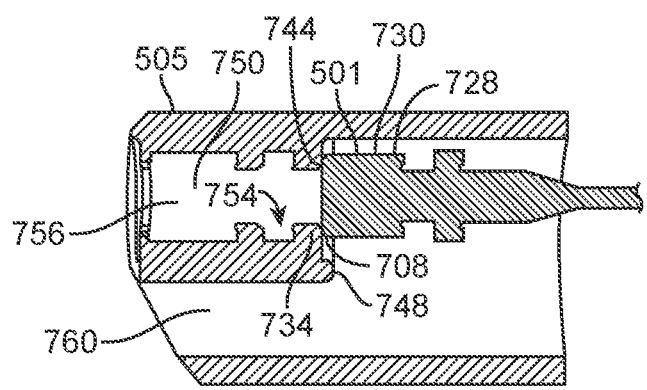
Figure 24C:
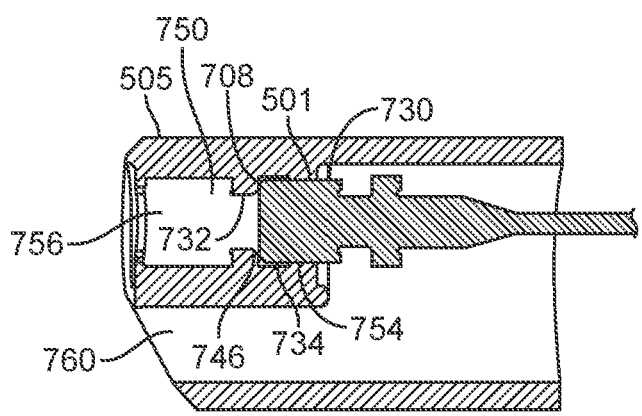
Figure 24D:
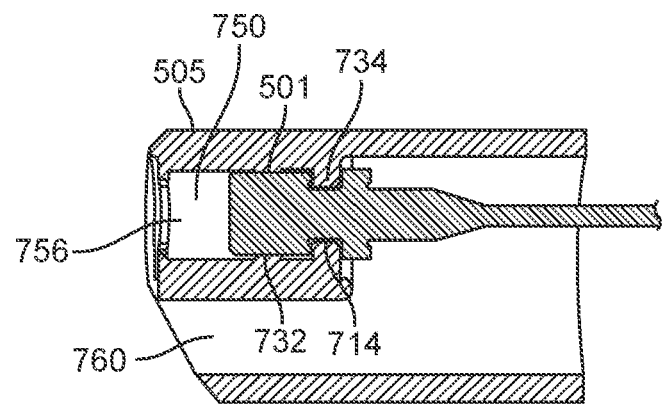
Figure 24E:
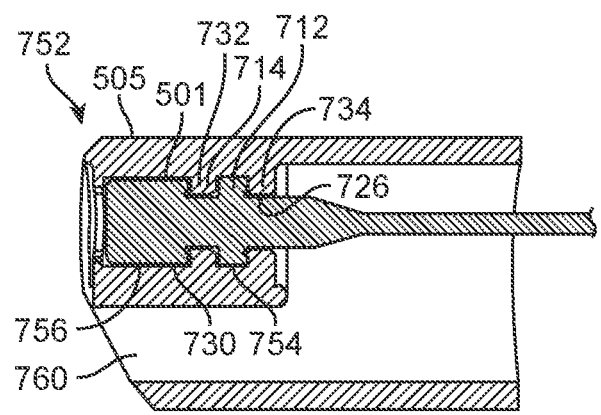

FIG. 24A-24E is a side cut away view of cartridge assembly and light tip shell showing the sequence of insertion steps resulting in the insertion of cartridge assembly 501 into light tip shell 505. In FIG. 24A, cartridge assembly 501 is positioned to be inserted into cartridge cavity 750 in order to create light tip assembly 752. In FIG. 24B, cartridge assembly 501 is brought into contact with light tip shell 505 at the lateral end of cartridge cavity 750, bringing lead bevel 708 on emitter retention ring 730 of cartridge assembly jacket 728 into contact with lateral shell insertion bevel 744 on lateral shell retention ring 734 of light tip shell 505. As illustrated in FIG. 24C, as cartridge assembly 501 moves into cartridge cavity 750, lateral shell retention ring 734 is compressed and pushed aside by emitter retention ring 730. In FIG. 24C, cartridge assembly 501 has moved into cartridge cavity 750 to a position where lead bevel 708 is in contact with medial shell insertion bevel 746 and the medial end of cartridge assembly 501 is at least partially positioned in shell lateral retention groove 754. As illustrated in FIG. 24D, as cartridge assembly 501 moves further into cartridge cavity 750 medial shell retention ring 732 is compressed and moved out of the way while lateral shell retention ring 734 moves into medial retention groove 714. As illustrated in FIG. 24E, once cartridge assembly 501 is fully seated in cartridge cavity 750 emitter retention ring 730 is positioned in emitter cavity 756, medial shell retention ring 732 is positioned in medial retention groove 714, cartridge assembly retention ring 712 is positioned in shell lateral retention groove 754 and lateral shell retention ring 734 is positioned in lateral retention groove 726.

As illustrated in FIGS. 24A through 24E, insertion of cartridge assembly 501 is facilitated by the interaction of the insertion bevels 744, 746, 708 and 758. As cartridge 501 is inserted the insertion bevels assist in aligning cartridge assembly 501 in cartridge cavity 750 such that the force on shell retention rings 732 and 734 is distributed evenly around the circumference of shell retention rings 732 and 734 and such that the force required to move retention rings 732 and 734 out of the way is reduced over what would be required without insertion bevels 744, 746, 708 and 758. As is further illustrated in FIGS. 24A through 24E, cartridge assembly 501 and cartridge cavity 750 are designed such that the features of cartridge assembly 501 encounter shell retention rings 732 and 734 sequentially such that cartridge assembly 501 may be moved into cartridge cavity 750 using only the force required to move aside and compress each shell retention ring individually. In particular, as illustrated in FIG. 24B, when emitter retention ring 730 encounters lateral shell retention ring 734, the force required to move cartridge assembly 501 into cartridge cavity 750 is the force required to compress lateral shell retention ring 734 and move it aside. When, as illustrated in FIG. 24C, emitter retention ring 730 encounters medial shell retention rings 732, lateral shell retention ring 734 has already been compressed and moved aside so the force required to continue to advance cartridge assembly 501 into cartridge cavity 750 is the force required to compress medial shell retention ring 734 and move it aside. When, as illustrated in FIG. 24D, cartridge assembly retention ring 712 encounters lateral shell retention ring 734, medial shell retention ring 732 has been compressed and moved aside so the force required to continue to advance cartridge assembly 501 into cartridge cavity 750 is the force required to compress lateral shell retention ring 734 and move it aside.

In embodiments of the invention, cartridge assembly retention ring 712 has a diameter greater than the diameter of emitter retention ring 730 thus, emitter cavity 756 may have a smaller diameter than shell lateral retention groove 754. In these embodiments, cartridge assembly retention ring 712 will not fit into emitter cavity 756, preventing cartridge assembly 501 from being inserted too deep into cartridge cavity 750.

In embodiments of the invention, cartridge assembly 501 may be removed from a light tip shell 505 by reversing the prior steps. In embodiments of the invention, it may be preferable to design a system such that the force required to remove light tip shell 505 from cartridge assembly 501 is greater than the force required attach light tip shell 505 to cartridge assembly 501. In practice, the higher removal force is desirable because, when a user wants to remove light tip shell 505 from their ear, they may do so by pulling on LT cable 20, creating significant stress and exerting forces which might result in cartridge assembly 501 separating from light tip shell 505 if the force required to separate those two parts was too low. Lower assembly forces are desirable because lower forces ease the manufacture of light tip assembly 752, reducing the manufacture time and reducing damage done during the manufacture process. Thus, in embodiments of the invention, elements of the invention increase the force needed to remove cartridge assembly 501 from light tip shell 505 once cartridge assembly 501 is fully positioned in light tip shell 505. In particular, with cartridge assembly 501 fully inserted into light tip shell 505, medial shell retention ring 732 is positioned in medial retention groove 714 and lateral shell retention ring 734 is positioned in lateral retention groove 726 as illustrated in FIG. 22. Removing cartridge assembly 501 from light tip shell 505 therefore requires more force than inserting cartridge assembly 501 into light tip shell 505 because of the presence of retention elements such as medial shell catch ring 738, which is positioned in medial undercut 720 and lateral shell retention ring 736, which is positioned in lateral undercut 718. Stabilizer ring 748 acts as an additional retention element. Removal of cartridge assembly 501 from light tip shell 505 is resisted by the presence of medial shell retention ring 732 in medial retention groove 714 and the presence of lateral shell retention ring 734 in lateral retention groove 726 since both of those retention rings would have to be compressed and/or moved out of the way simultaneously as cartridge assembly 501 is removed. Removal of cartridge assembly 501 would be further resisted by medial shell catch ring 738 catching on medial jacket catch ring 742 and by lateral shell catch ring 736 catching on lateral jacket catch ring 740. Removal of cartridge assembly 501 would be further resisted by the presence of medial shell retention ring 732 which would increase the force required to bend lateral shell retention ring 734 out of the way of cartridge assembly retention ring 712 when the components are separated.

In contrast to the insertion of cartridge assembly 501 into cartridge cavity 750, the removal of cartridge assembly 501 from cartridge cavity 750 requires sufficient force to compress and move both lateral shell retention ring 734 and medial shell retention ring 732 out of the way simultaneously. As illustrated in FIG. 24E, removal of cartridge assembly 501 from cartridge cavity 750 would require cartridge assembly retention ring 712 to compress and move aside lateral shell retention ring 734 while emitter retention ring 730 simultaneously compresses and moves aside medial shell retention ring 732. Thus, the force required to remove cartridge assembly 501 from cartridge cavity 750, when cartridge assembly 501 is fully inserted into cartridge cavity 750 may be at least twice the force required to insert cartridge assembly 501 into cartridge cavity 750. This force may be further increased by, for example, the interaction of retention rings and catch rings as described above.

In embodiments of the invention, the cartridge assembly jacket may be made of, for example, a silicon material, such as, for example Biopor. In embodiments of the invention, LT cable 20 may be a low durometer material. The use of a low durometer material facilitates the use of a replacement cable in either ear of a user, without requiring a specific cable for the left or right ear as would be the case for a high durometer or formed cable. The use of a low durometer LT cable thus enables the health care professional to maintain a single set of replacement cables, rather than a set for the right ear and a separate set for the left ear.

Figure 25:
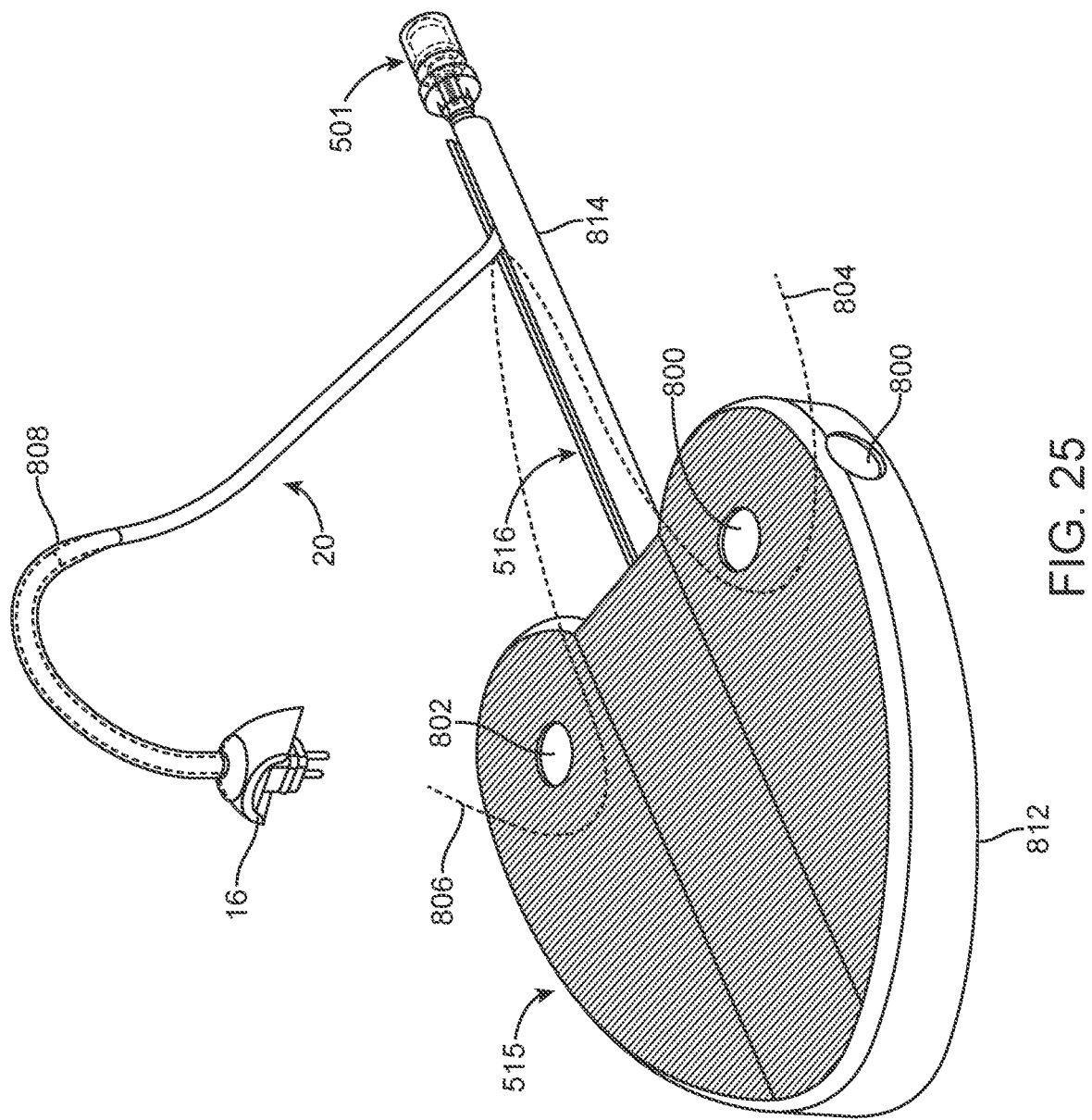
FIG. 25 is a perspective view of an insertion tool and LT cable according to one embodiment of the present invention.
Figure 26:
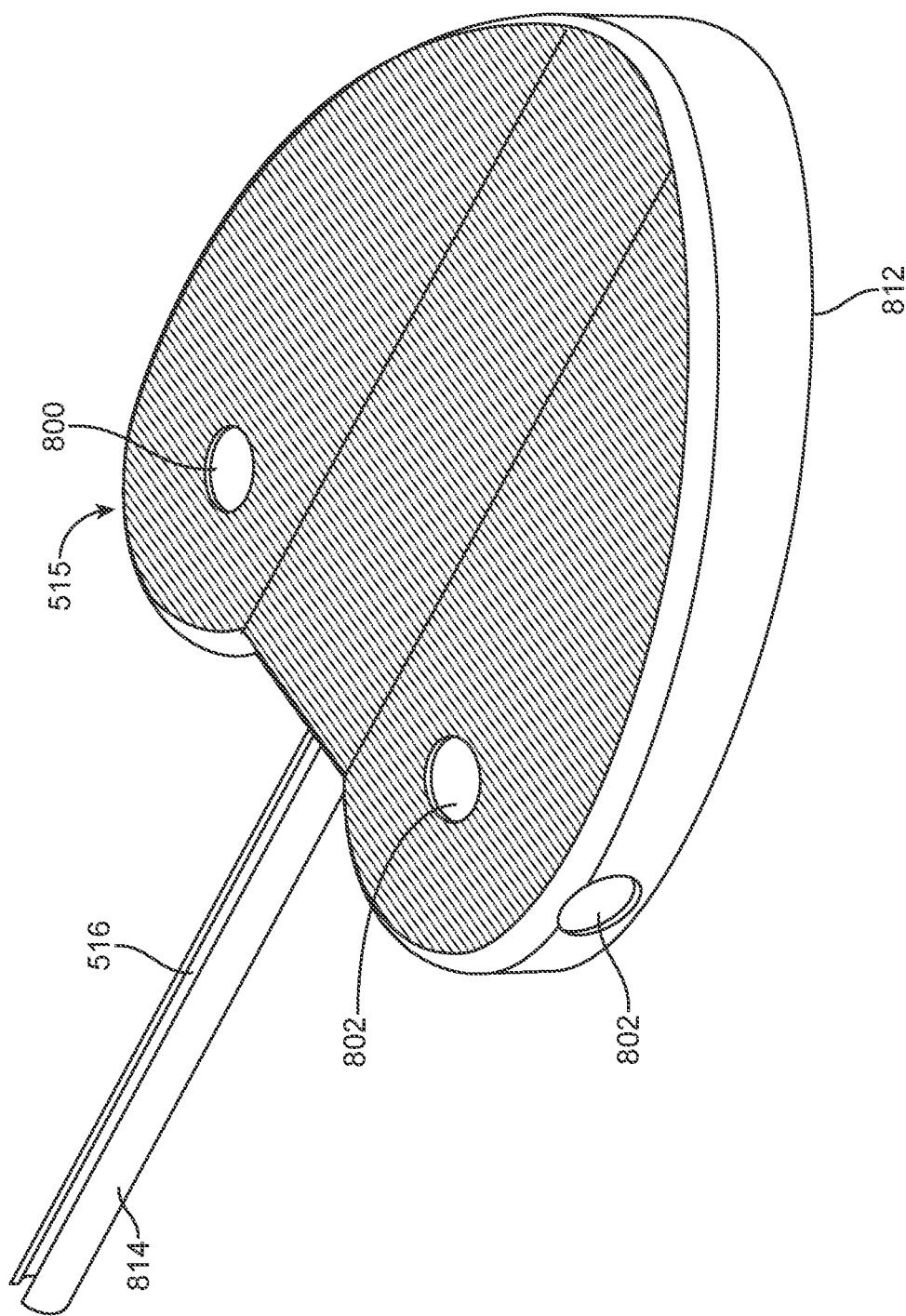
FIG. 26 is a perspective view of an insertion tool according to one embodiment of the present invention.

FIGS. 25 and 26 are perspective views of an insertion tool and LT cable according to one embodiment of the present invention. In FIGS. 25 and 26, insertion tool 515 includes handle 812 and insertion tube 814. Handle 812 includes left guide markers 800 and right guide markers 802. Insertion tube 814 includes tool groove 516. Tool groove 516 may be adapted to receive LT cable 20 in order to facilitate the positioning of cartridge assembly 501 in light tip shell 505 as illustrated in FIGS. 24A-E. In the insertion sequence illustrated in FIGS. 24 A-E, the insertion of cartridge assembly 501 into light tip shell 505 may be accomplished and facilitated using insertion tool 515, in which case, the medial end of insertion tool 515 may (e.g. between the step illustrated in FIG. 24D and the step illustrated in FIG. 24E) enter emitter cavity 756.

In embodiments of the invention, the insertion tool orients the cartridge assembly 501, including emitter 290 and light tip shell 505 to obtain an optimal insertion angle (note that LT cable 20 is universally adaptable but LT shells 505 are designed to be either right or left). The angle of insertion is important to minimize the stress of insertion and the angle is controlled by the insertion tool. Blue dots and red dots help with orientation. The medial end of insertion tool 515 may conform to the geometry of the lateral end of the cartridge assembly jacket to minimize stresses on the cartridge assembly jacket by distributing forces evenly.

In embodiments of the invention with cartridge assembly 501 positioned in the medial end of tool groove 516, LT cable 20 may be properly positioned for insertion by using either left guide marker 800 to align LT cable 20 along left alignment path 804 or right guide marker 802 to align LT cable 20 along right alignment path 806.

In embodiments of the invention, LT cable 20 may include integrated stiffener 808 to increase the durometer (stiffness) of LT cable 20 at a medial end, close to BTE connector 16. Integrated stiffener 808 may be used to decouple gravitational forces acting on BTE 18 from forces acting on light tip assembly 752. In embodiments of the invention, LT cable 20 is a dual durometer cable having a first durometer at an end adjacent light tip assembly 752 and a second, higher durometer at a second end adjacent BTE connector 16.

In embodiments of the invention, emitter 290 may be replaced with a conventional hearing aid receiver, allowing emitter 290 to be swapped with a conventional receiver in the eartip. The ability to swap out the emitter for a conventional receiver would provide a health care provider with an alternative to the emitter for situations where a conventional receiver would be beneficial. For example, where there was a failure in a light activated component of the hearing aid, enabling the health care professional to provide the user with a working hearing aid until the failed light activated component could be repaired.

In embodiments of the invention, the invention comprises a replaceable ear tip including a medial opening, a lateral opening, a central opening, a spine at a superior side of the central opening and a cable channel running from the medial opening to the lateral opening through the spine. In embodiments of the invention, the cable channel includes a cylindrical bore at a medial end of the cable channel, a lobe shaped opening connected to the cylindrical bore and a cable groove extending from the lobe shaped opening to the lateral opening through the spine. In embodiments of the invention, a superior slot extends from a superior surface of the ear tip to the cable groove and from the lateral opening of the light tip to a central point of the ear tip. In embodiments of the invention, an inferior slot extends from the cable grove to an inferior surface of the ear tip spine.

In embodiments of the invention, the invention comprises a replaceable ear tip including a cartridge cavity including an emitter cavity and at least one retention groove lateral to the cartridge cavity. In embodiments of the invention, a first compressible retention ring is positioned between the emitter cavity and a first retention groove. In embodiments of the invention, the replaceable eartip includes a second compressible retention ring lateral to the first retention groove. In embodiments of the invention, the replaceable ear tip further includes an acoustic vent extending from a lateral to a medial end of the replaceable ear tip. In embodiments of the invention, the replaceable ear tip further includes a stabilizer ring attached at a lateral face of the second compression ring. In embodiments of the invention, the replaceable ear tip further includes at least one catch ring on a medial surface of the first or second compression ring. In embodiments of the invention, the replaceable ear tip further includes a first catch ring on a medial surface of the first compression ring and a second catch ring on a medial surface of the second compression ring. In embodiments of the invention, the replaceable ear tip further includes at least one bevel on a lateral surface of the first or second compression ring. In embodiments of the invention, the replaceable ear tip further includes a first bevel on a lateral surface of the first compression ring and a second bevel on a lateral surface of the second compression ring.

In embodiments of the invention, the invention comprises a light tip cable including a cartridge assembly affixed to a medial end of the cable, the cartridge assembly including an emitter housing where the emitter housing includes an opening at a medial end of the housing and a flange at a lateral end of the housing. In embodiments of the invention, the cartridge assembly includes a light emitting element in the housing extending to the opening, retention features covering at least a portion of the housing, including the flange, the retention features comprising a lateral face and a lobe and at least one load bearing strand extending from the cable to the emitter; and electrical connectors extending from the cable to the light emitting element. In embodiments of the invention, the cartridge assembly includes an emitter housing wherein the emitter housing includes an emitter opening at a medial end of the housing and a jacket extending from the emitter opening to a cable opening at a lateral end of the jacket. In embodiments of the invention, an emitter is positioned at a medial end of the emitter housing, a first retention ring surroundes the emitter, a second retention ring is positioned lateral to the first retention ring and a retention groove between the first and second retention rings. In embodiments of the invention, the cartridge assembly further includes at least one catch ring on the first or second retention rings. In embodiments of the invention, the cartridge assembly further includes a first catch ring on the first retention ring and a second catch ring on the second retention ring. In embodiments of the invention, the cartridge assembly further includes at least one bevel on a medial surface of the first or second retention rings. In embodiments of the invention, the cartridge assembly further includes a first bevel on a medial surface of the first retention ring and a second bevel on a medial surface of the second retention ring.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth hereinbelow not be construed as being order-specific unless such order specificity is expressly stated in the claim.

REFERENCE NUMBERS

| Number | Element |
|---|---|
| 10 | LT Housing |
| 12 | Light Tip Connector |
| 14 | Internal Assembly |
| 16 | BTE Connector |
| 18 | BTE |
| 20 | LT Cable |
| 30 | LT Electrode |
| 40 | Guide Channel |
| 42 | Channel Guides |
| 45 | Guide Pins |
| 50 | Locking Pin 50 |
| 60 | Pogo Pin Electrode |
| 70 | Latch |
| 72 | Latch Hook |
| 74 | Latch and locking pin assembly |
| 80 | Wire Channel |
| 90 | Wires |
| 92 | Wires |
| 100 | BTE Housing |
| 110 | Pogo Pin Electrode |
| 120 | Contact Tip |
| 200 | Tympanic Lens |
| 210 | Hearing Aid System |
| 220 | Hearing Device |
| 222 | Light Tip |
| 230 | Audio Processor |
| 240 | Light Pulses |
| 290 | Emitter |
| 340 | Sound |
| 310 | Microphone |
| 320 | Analog to Digital Converter |
| 330 | Digital Signal Processor |
| 420 | Umbo Lens |
| 430 | Photodetector |
| 440 | Microactuator |
| 501 | Cartridge Assembly |
| 505 | Light Tip Shell |
| 506 | Cylindrical Bore |
| 507 | Step |
| 508 | Lobe Shaped Opening |
| 509 | Back Stop |
| 510 | Cable Groove |
| 511 | Superior Slot |
| 512 | Inferior Slot |
| 513 | Continuous Slot |
| 514 | Teardrop Feature |
| 515 | Insertion/Removal Tool |
| 516 | Tool Groove |
| 517 | Counterbored Feature |
| 520 | Emitter Housing |
| 521 | Load Bearing Strand |
| 522 | Cable Conductors |
| 523 | Cable Retention Feature |
| 544 | Retention Features |
| 601 | Medial End of Light Tip Shell |
| 602 | Flange |
| 603 | Lobe |
| 604 | Lateral face of retention feature |
| 605 | Lateral End of Light Tip Shell |
| 606 | Inferior side of spine of light tip |
| 607 | Light Tip Shell Spine |
| 608 | Lateral End of Inferior Slot |
| 609 | Superior side of light tip shell |

-continued

| Number | Element |
|---|---|
| 610 | Handle |
| 612 | Extension |
| 614 | Medial End of Inferior Slot |
| 700 | Jacket (silicon/biopor) |
| 702 | Booster Ring |
| 704 | Handle |
| 706 | Emitter Opening |
| 708 | Lead Bevel |
| 710 | Emitter post |
| 712 | Cartridge Assembly Retention Ring |
| 714 | Medial Retention Groove |
| 716 | Lateral Ramp (Lead-in Adhesive Layer)/Lead in for insertion tool |
| 718 | Lateral Undercut |
| 720 | Medial Undercut |
| 722 | Lateral Taper |
| 724 | Retention Ring Bevel |
| 726 | Lateral Retention Groove |
| 728 | Cartridge Assembly Jacket |
| 730 | Emitter Retention Ring |
| 732 | Medial Shell Retention Ring |
| 734 | Lateral Shell Retention Ring |
| 736 | Lateral Shell Catch Ring |
| 738 | Medial Shell Catch Ring |
| 740 | Lateral Jacket Catch Ring |
| 742 | Medial Jacket Catch Ring |
| 744 | Lateral Shell Insertion Bevel |
| 746 | Medial Shell Insertion Bevel |
| 748 | Stabilizer Ring |
| 750 | Cartridge Cavity |
| 752 | Light Tip Assembly |
| 754 | Shell Lateral Retention Groove |
| 756 | Emitter Cavity |
| 758 | Lateral Bevel |
| 760 | Acoustic Vent |
| 800 | Left Guide Marker |
| 802 | Right Guide Marker |
| 804 | Left Alignment Path |
| 806 | Right Alignment Path |
| 808 | Integrated Stiffener |
| 812 | Handle |
| 814 | Insertion Tube |

What is claimed is:

1. An ear tip cartridge assembly comprising:
an ear tip including
a cartridge assembly cavity having an assembly retention cavity and at least one retention groove lateral to the cartridge assembly cavity,
a first compressible retention ring between the assembly retention cavity and a first retention groove, and
a second compressible retention ring lateral to the first retention groove;
a cartridge assembly housed within the cartridge assembly cavity of the ear tip, the cartridge assembly including at least one retention ring and an emitter affixed to a cable configured to be connected to an audio processor; and
wherein the at least one retention ring of the cartridge assembly is coupled with the at least one retention groove of the ear tip.

2. The ear tip cartridge assembly according to claim 1, wherein the emitter is an infrared laser.

3. The ear tip cartridge assembly according to claim 1, wherein the emitter is an electromagnetic transmitter.

4. The ear tip cartridge assembly according to claim 1, further comprising at least one load bearing strand extending from the cable to the emitter.

5. The ear tip cartridge assembly according to claim 4, wherein the at least one load bearing strand is made of Kevlar.

6. The ear tip cartridge assembly according to claim 1, further comprising a stabilizer ring attached at a lateral face of the second compression ring.

7. The ear tip cartridge assembly according to claim 1, wherein the ear tip further comprises an acoustic vent.

8. The ear tip cartridge assembly according to claim 1, wherein a force required to remove the cartridge assembly from the cartridge assembly cavity is at least twice a force required to insert the cartridge assembly into the cartridge assembly cavity.

9. An ear tip cartridge assembly comprising:
an ear tip including
a cartridge assembly cavity having an assembly retention cavity and at least one retention groove lateral to the cartridge assembly cavity,
a first compressible retention ring between the assembly retention cavity and a first retention groove, and
a second compressible retention ring lateral to the first retention groove;
a cartridge assembly housed within the cartridge assembly cavity of the ear tip, the cartridge assembly including
a cartridge assembly jacket having an emitter cavity including an emitter retention groove and at least one retention ring lateral to the emitter cavity,
an emitter affixed to a cable configured to be connected to an audio processor, the emitter having a flange coupled with the emitter retention groove of the cartridge assembly jacket; and
wherein the at least one retention ring of the cartridge assembly jacket is coupled with the retention groove of the ear tip.

10. The ear tip cartridge assembly according to claim 9, wherein the cartridge assembly jacket further comprises a lead bevel covering at least a portion of a distal end of the emitter.

11. The ear tip cartridge assembly according to claim 9, wherein the emitter is an infrared laser.

12. The ear tip cartridge assembly according to claim 9, wherein the emitter is an electromagnetic transmitter.

13. The ear tip cartridge assembly according to claim 9, further comprising at least one load bearing strand extending from the cable to the emitter.

14. The ear tip cartridge assembly according to claim 13, wherein the at least one load bearing strand is made of Kevlar.

15. The ear tip cartridge assembly according to claim 9, further comprising a stabilizer ring attached at a lateral face of the second compression ring.

16. The ear tip cartridge assembly according to claim 9, wherein the ear tip further comprises an acoustic vent.

17. The ear tip cartridge assembly according to claim 9, wherein a force required to remove the cartridge assembly from the cartridge assembly cavity is at least twice a force required to insert the cartridge assembly into the cartridge assembly cavity.

* * * * *